(12) United States Patent
Zakeeruddin et al.

(10) Patent No.: US 7,932,404 B2
(45) Date of Patent: Apr. 26, 2011

(54) 2,2-BIPYRIDINE LIGAND, SENSITIZING DYE AND DYE SENSITIZED SOLAR CELL

(75) Inventors: Shaik Mohammad Zakeeruddin, Renens (CH); Cédric Klein, Lausanne (CH); Peng Wang, Lausanne (CH); Michaël Graetzel, St-Sulpice (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 1007 days.

(21) Appl. No.: 11/658,780

(22) PCT Filed: Jul. 29, 2005

(86) PCT No.: PCT/CH2005/000452
§ 371 (c)(1),
(2), (4) Date: Mar. 28, 2007

(87) PCT Pub. No.: WO2006/010290
PCT Pub. Date: Feb. 2, 2006

(65) Prior Publication Data
US 2009/0000658 A1  Jan. 1, 2009

(30) Foreign Application Priority Data

Jul. 29, 2004 (CH) .................... 04405484.9

(51) Int. Cl.
*C07D 495/02* (2006.01)
*H01M 6/32* (2006.01)

(52) U.S. Cl. ............ 549/50; 549/51; 136/244; 136/256; 429/111; 257/E27.124; 257/E31.126; 257/E51.015; 257/E51.027

(58) Field of Classification Search .................... 549/51, 549/50; 136/244, 256; 429/111; 257/E27.124, 257/E31.126, E51.015, E51.027
See application file for complete search history.

(56) References Cited

U.S. PATENT DOCUMENTS

| 4,927,721 A | 5/1990 | Gratzel et al. | |
| 5,250,644 A * | 10/1993 | Tokunaga et al. | ............. 526/318 |

FOREIGN PATENT DOCUMENTS

| EP | 0 333 641 | 9/1989 |
| EP | 1 087 412 | 3/2001 |
| EP | 1 091 373 | 4/2001 |
| WO | WO 91/16719 | 10/1991 |
| WO | WO 94/04497 | 3/1994 |
| WO | WO 95/18456 | 7/1995 |
| WO | WO 95/29924 | 11/1995 |

OTHER PUBLICATIONS

P. Wang, S.M. Zakeeruddin, J.E. Moser, M.K. Nazeeruddin, et al., "A stable quasi-solid-state dye-sensitized solar cell with an amphiphilic ruthenium sensitizer and polymer gel electrolyte", Nature Materials, vol. 2, (Jun. 2003).*
P. Wang, S.M. Zakeeruddin, P. Comte, R. Charvet et al., "Enhance the Performance of Dye-Sensitized Solar Cells by Co-grafting Amphiphilic Sensitizer and Hexadecylmalonic Acid on TiO2 Nanocrystals", J. Phys. Chem. B. vol. 107. No. 51 (2003).*
M.K. Nazeeruddin, P. Pechy, T. Renouard, S.M. Zakeeruddin, et al., Engineering of Efficient Panchromatic Sensitizers for Nanocrystalline TiO2-Based Solar Cells, American Chemical Society vol. 123, No. 8, 1613-1624 (2001).
S.M. Zakeeruddin, K. Nazeeruddin, R. Humphry-Baker, P. Pechy, et al. Design, Synthesis, and Application of Amphiphilic Ruthenium Polypyridyl Photosensitizers in Solar Cells Based on Nanocrystalline TiO2 Films, Langmuir, vol. 18, No. 3 (2002).
P. Wang, S.M. Zakeeruddin, J.E. Moser, M.K. Nazeeruddin, et al., A stable quasi-solid-state dye-sensitized solar cell with an amphiphilic ruthenium sensitizer and polymer gel electrolyte, Nature Materials, vol. 2, (Jun., 2003).
P. Wang, S.M. Zakeeruddin, P. Comte, R. Charvet et al., Enhance the Performance of Dye-Sensitized Solar Cells by Co-grafting Amphiphilic Sensitizer and Hexadecylmalonic Acid on TiO2 Nanocrystals, J. Phys. Chem. B, vol. 107, No. 51 (2003).
L.E. Bouder et al., Hydroxy-Functionalized Bipyridine and Tris(bipyridine) metal Chromophores: Synthesis and Optical Properties, Eur. J. Org. Chem, pp. 3024-2033 (2002).
C.R. Leidner, et al., Synthesis and electropolymerization of distyrylbipyridine and methyldistyrylbipyridine complexes of iron, ruthenium, osmium, rhenium, and cobalt; Inorganic Chemistry, 26(6), p. 883, col. 1, table 1.
M. Bougault, et al., Beilstein Institute for Organic Chemistry, Frankfurt-Main, DE, 1998, Can. J. Chem., vol. 75, No. 3, pp. 318-325 (1997).
Sasse et al., Beilstein Institute for Organic Chemistry, Frankfurt-Main, DE 1988, J. Chem. Soc, pp. 1347-1349 (1961).
P.D. Beer et al., Syntheses, coordination, spectroscopy and electropolymerization studies of new alkynyl and vinyl linked benzo- and aza crown ether-bipyridyl ruthenium (II) complexes. Spectrochemical Recognition of Group IA/IIA metal cations; Chemical Abstracts Service.
Andre-Jean Attias et al., Tuning of the Mesogenic, Electronic, and Optical Properties of New Conjugated 3,3'-Bipyridine Derivatives, Abstract & Chemisty of Materials, 12(2), 461-471, (2000).

* cited by examiner

*Primary Examiner* — Ling-Siu Choi
(74) *Attorney, Agent, or Firm* — Clifford W. Browning; Krieg DeVault LLP

(57) ABSTRACT

A dye sensitized solar cell, comprising a-heteroleptic polypyridil complex of Ru, Os or Fe. The donating ligand has an extended conjugated n-system increasing the light absorbance and keeing the LUMO energy level higher than that of the anchoring ligand. A compacting compound whose molecular structure comprises a terminal group, a hydrophobic part and an anchoring' group may be co-adsorbed together with the dye on the semi-conductive metal oxide layer of the photoanode, forming a dense mixed self-assembled monolayer.

17 Claims, 12 Drawing Sheets

Z910

K60

2,2-BIPYRIDINE LIGAND, SENSITIZING DYE AND DYE SENSITIZED SOLAR CELL

The present invention concerns an organic compound. The present invention further concerns a sensitizing dye incorporating said organic compound. Still further, the present invention concerns a dye-sensitized solar cell.

Dye-sensitized solar cells, or DSSCs, are regenerative photo-electrochemical cells comprising a photoanode, said photoanode comprising at least one semiconductive metal oxide layer on a conductive substrate, sensitized by at least one chromophoric substance, a counter-electrode, and an electrolyte positioned between these electrodes.

In cells of this type, at least one of these electrodes is sufficiently transparent or translucent for allowing light input. The afore-said semi-conductive metal oxide layer is conveniently made of oxides of transition metals or elements either of the third main group, or of the fourth, fifth and sixth sub-groups of periodic table of elements, the surface of the photoanode in contact with the electrolyte being porous, with a porosity factor of preferably at least 20. The "porosity factor" is defined as the ratio of the photo-electrochemically active surface of the photoanode to the surface area of the substrate covered by the layer(s) of semiconductive metal oxide. The use of nanocrystalline titanium dioxide was shown to be particularly advantageous. The term "nanocrystalline" means that the semiconductive metal oxide, in particular $TiO_2$, is in polycrystalline form with a granulometry of the order of several nanometers, for example 10 to 50 nanometers.

In this type of cell, a chromophoric substance, often called photosensitizer or photosensitizing dye, forms a substantially monomolecular layer attached to the semiconductive metal oxide layer, in particular the nanocrystalline $TiO_2$ layer. The chromophoric substance may be bound to the metal oxide layer by means of anchoring groups like carboxylate or phosphonate or cyano groups or chelating groups with π-conducting character like oxymes, dioxymes, hydroxyquinolines, salicylates and (-keto-enolates. Several transition metal complexes, in particular ruthenium complexes, but also osmium or iron complexes, with heterocyclic ligands like bidentate, tridentate or polydentate polypyridil compounds, have been shown to be efficient photosensitizing dyes. Sensitizing dyes and cells of this type are described inter alia in EP 0333641, EP 0525070, EP 0613466 and EP 0758337.

The mesoporous texture of the $TiO_2$ film in these cells significantly increases the cross section of light harvesting by surface-anchored charge transfer sensitizers while maintaining a good contact with electrolytes. In these photovoltaic devices, ultrafast electron-injection from a photoexcited dye into the conduction band of an oxide semiconductor, and subsequently dye regeneration and hole transportation to the counter electrode, are responsible for the efficient generation of electricity.

Among suitable electrolytes are those including a redox system consisting of a mixture of at least one electrochemically active salt and at least one molecule designed to form an oxidation-reduction system with either the anion or cation of the said salt. Electrolytes wherein said electrochemically active salt has a melting point below ambient temperature or forms with the afore-said molecule a phase with a melting point below ambient temperature have been described in EP 0737358. Additionally, gelified materials incorporating triiodide/iodide as a redox couple, as disclosed by EP 1087412, were introduced to substitute the liquid electrolytes by quasi-solid state materials.

A respectable 10.4% light-to-electricity conversion efficiency at AM 1.5 solar irradiance has been obtained for photovoltaic devices with a panchromatic dye and a liquid electrolyte containing the triiodide/iodide couple, as reported in J. Am. Chem. Soc. 123, 1613-1624 (2001).

However the achievement of long-term stability at temperatures of 80–85° C., which is an important requirement for outdoor application of the DSSC, still remains a major challenge:

The leakage of liquid electrolyte from such DSSC modules, possible desorption of loosely attached dyes and photodegradation in the desorbed state, as well as corrosion of the photoelectrode and/or counter electrode by the triiodide/iodide couple, may be considered as some critical factors limiting the long-term performance of the DSSC, especially at elevated temperature. A particular problem of stability at 80° C. in DSSCs containing the iodide/triiodide redox couple, upon aging, is the drop in open circuit potential ($V_{oc}$), causing the poor stability. It is believed that the dark current of DSSCs increases and $V_{oc}$ decreases, due to the interaction of triiodide with bare zones of the $TiO_2$ electrode, that is not completely covered with dye molecules.

Grätzel and co-workers demonstrated (Langmuir (2002) 18, 952) that heteroleptic amphiphilic complexes of formula RuLL'$(NCS)_2$, where L is the anchoring ligand 4,4'-dicarboxy -2,2'-bipyridine and L' is a 2,2'-bipyridine substituted by one or 2 long alkyl chains, are an interesting class of sensitizing dyes for DSSCs. The long alkyl chains in all likelihood interact laterally to form an aliphatic network, thereby impeding triiodide from reaching the $TiO_2$ surface, resulting in increased open circuit potential of the cell and enhanced stability versus time. They further found (Nature Materials (2003) 2, 402) that a cell using the sensitizer cis-(NCS)$_2$RuLL', where L'=4,4'-dynonyl-2,2'-bipyridine, hereinafter referred to as Z907, in conjunction with a quasi solid state polymer gel electrolyte reaches an efficiency of >6% in full sunlight (air mass 1.5, 100 mW. $cm^{-2}$) with unprecedented stable performance under both thermal stress and soaking with light.

A further remarkable increase in photovoltaic performance was achieved by co-grafting hexadecylmalonic acid (HDMA) with Z907 sensitizing dye onto nanocrystalline $TiO_2$ films (J. Phys. Chem. B (2003) 107, 14336). Like Z907, HDMA contains two carboxylate groups to anchor it on the $TiO_2$ surface. Co-grafting of the two amphiphiles results in the formation of a mixed monolayer which should be more tightly packed than when the sensitizing dye is adsorbed alone, providing a more effective insulating barrier for the back electron transfer from $TiO_2$ conduction band to triiodide in the electrode. Retarding this unwanted redox process by the hydrophobic spacer reduces the dark current and increases the open circuit voltage of the solar cell. The cell also showed good stability under light soaking at 55° C. in simulated sunlight.

However, the molar extinction coefficient of known amphiphilic polypyridyl ruthenium sensitizers is lower than the one of N-719, the most efficient sensitizer for dye-sensitized solar cells. Additionally, the spectral response is blue-shifted compared with this most efficient sensitizing dye. Thus, the aim of the invention is to improve the light-harvesting capacity of amphiphilic sensitizing dyes by a rational design of the molecule while not decreasing their LUMO energy, allowing a high quantum efficiency of electron injection without lowering the conduction band of the mesoporous semiconductor and thus having a loss of device photovoltage.

These aims are achieved by using, as a ligand, an organic compound L1 having a formula selected from the group of formulae (a) to (j)

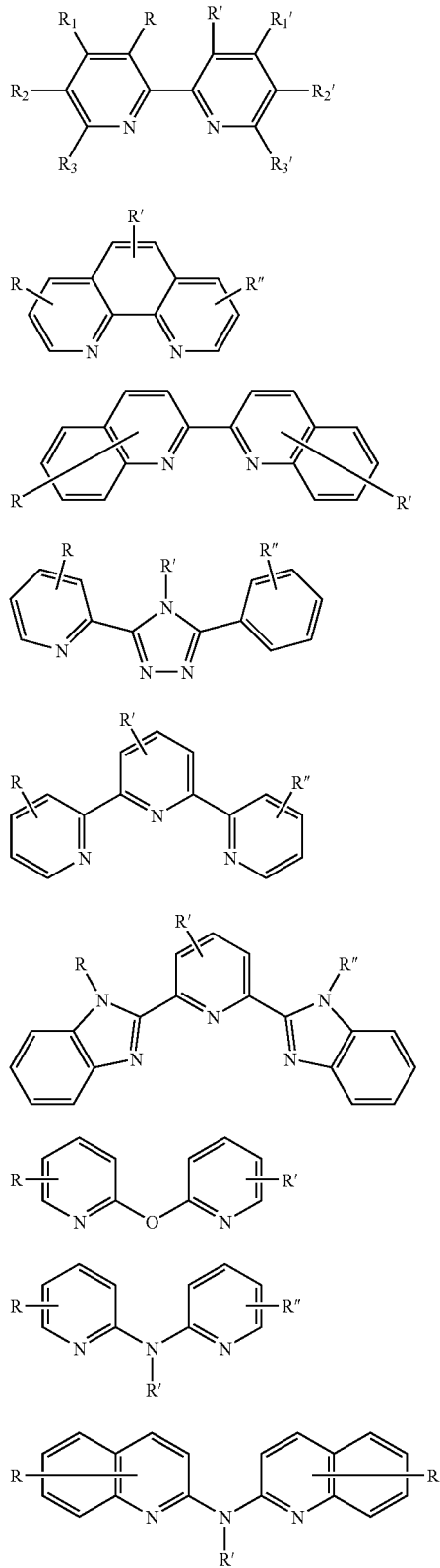

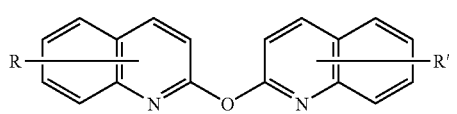

wherein at least one of substituents —R, —$R_1$, —$R_2$, —$R_3$, —R', —$R_1$', —$R_2$', —$R_3$', —R" comprises an additional π system located in conjugated relationship with the primary π system of the bidentate or respectively tridentate structure of formulae (a) to (j).

Briefly speaking, use of compounds L1 permits to extend the conjugated π system of the donating ligand, increasing the light absorbance and keeing the LUMO energy level higher than that of the anchoring ligand.

In preferred compounds L1, the said substituent is of the type

—R=[Π]—(Ral)$_q$ wherein —[Π]— represents schematically the π system of the aforesaid substituent, Ral represents an aliphatic substituent with a saturated chain portion bound to the π system, and wherein q represents an integer, indicating that —[Π]— may bear more than one substituent Ral.

The π system —[Π]— may be an unsaturated chain of conjugated double or triple bonds of the type wherein p is an integer from 1 to 8.

or an aromatic group Rar of from 6 to 22 carbon atoms, or a combination thereof.

The presence of an aromatic group is preferred, since it is less sensitive to oxidation than a long chain of conjugated double or triple bonds.

Among suitable aromatic groups, there are monocyclic aryls like benzene and annulenes, oligocyclic aryls like biphenyl, naphthalene, biphenylene, azulene, phenanthrene, anthracene, tetracene, pentacene, or perylene. The cyclic structure of Rar may incorporate heteroatoms.

Preferred ligands according to the invention are organic compounds L1 having a formula selected from the group of formulae (a) to (j)

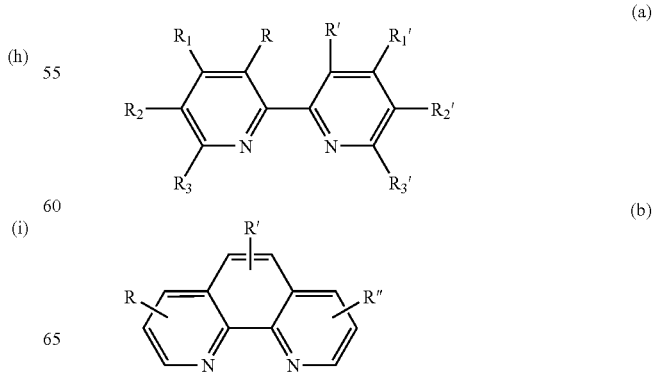

-continued (c) 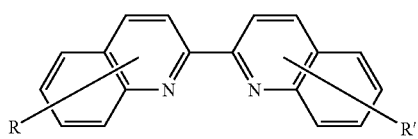

(d) 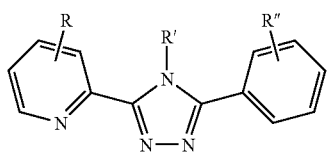

(e) 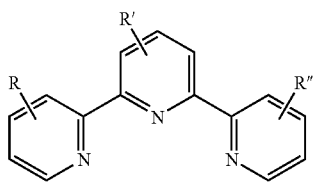

(f) 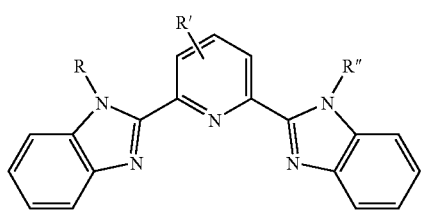

(g) 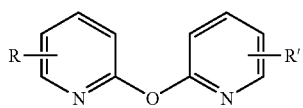

(h) 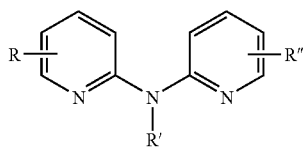

(i) 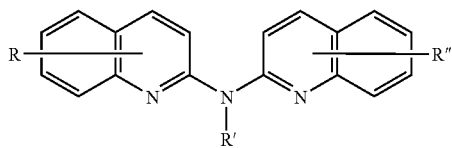

(j) 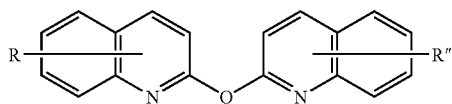

wherein at least one of substituents —R, —$R_1$, —$R_2$, —$R_3$, —R', —$R_1$', —$R_2$', —$R_3$', —R" is of formula (1), (2) or (3)

(1) 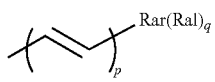

(2) 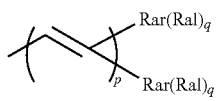

(3) 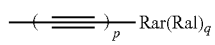

wherein p is an integer from 1 to 4,
wherein q is an integer from 1 to 4,
wherein Rar is a monocyclic or oligocyclic aryl from C6 to C22,
wherein —Ral is H, —R1, (—O—R1)$_n$, —N(R1)$_2$, —NHR1,

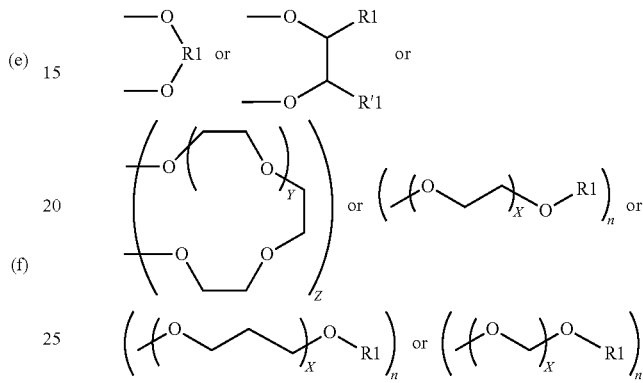

wherein R1, R'1 is an alkyl from 1 to 10 carbon atoms, $20 \geq X \geq 0$, and $5 \geq n \geq 0$, $8 \geq Y \geq 1$, Z=1 or 2, and
wherein the other one(s) of substituent(s) —R, —$R_1$, —$R_2$, —$R_3$, —R', —$R_1$', —$R_2$', —$R_3$', —R" is (are) the same or a different substituent of formula (1), (2) or (3), or is (are) selected from —H, —OH, —$R_2$, —$OR_2$ or —$N(R_2)_2$, wherein $R_2$ is an alkyl of 1 to 20 carbon atoms.

Compounds L1, in which p=1 are preferred, because the molecular structure is more rigid, less sensitive to oxidation, but is still an electron donator.

The invention faces more particularly compounds L1, wherein said compound is a 4,4'-disubstituted bipyridine of formula (a') 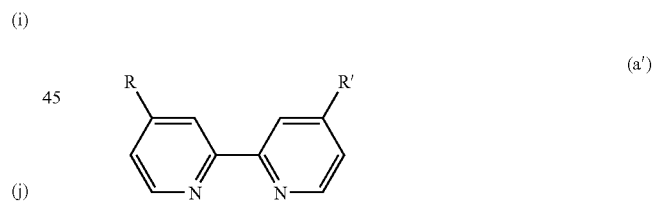

wherein p=1;
more particularly compounds L1, wherein R=R', p=1, and wherein Rar is selected from the group consisting of benzene, naphthalene and anthracene.

Particularly preferred compounds L1 are:
4,4'-bis(4-hexyloxystyryl)-2,2' bipyridine,
4,4'-bis(4-hexyloxynaphtalene-1-vinyl)-2,2' bipyridine,
and 4,4'-bis[4-(1,4,7,10-Tetraoxyundecyl)styryl]-2,2'-bipyridine].

FIGS. 11 and 12 show further examples 1 to 10 of L1 compounds.

The resulting sensitizing dye is an organometallic complex of a metal Me selected from the group consisting of Ru, Os and Fe, comprising as a ligand a compound L1 as described herein before, said complex being of formula Me L1 L(Z)$_2$ (I)

if L1 is a compound of formula (a'), (b), (c), (d), (g), (h), (i) or (j)

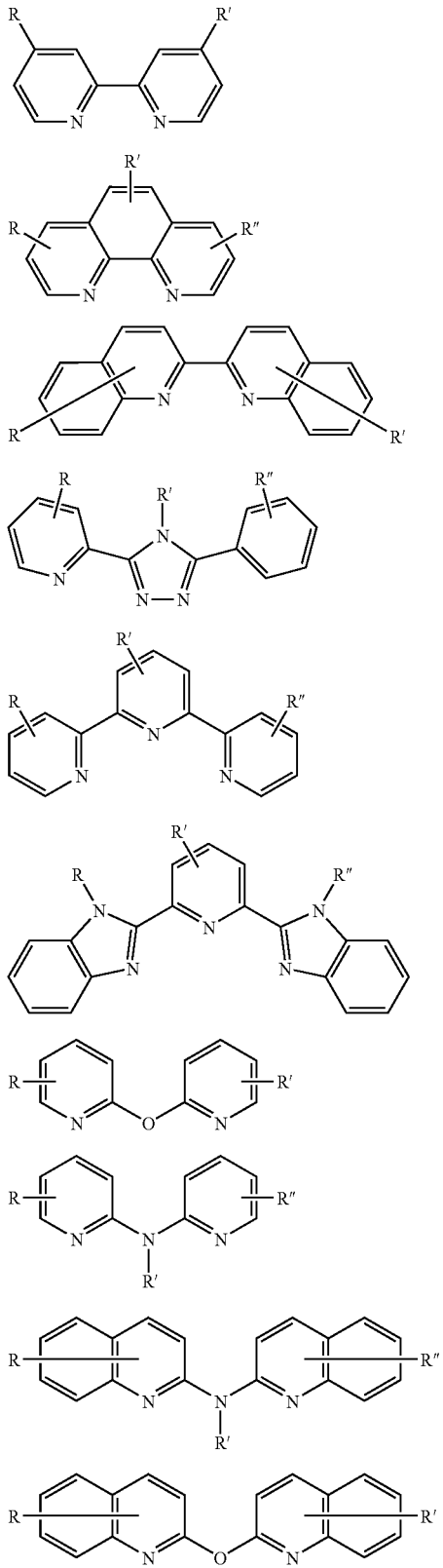

and of formula $$Me\ L1\ L\ Z \quad (II)$$

if L1 is a compound of formula (e) or (f)

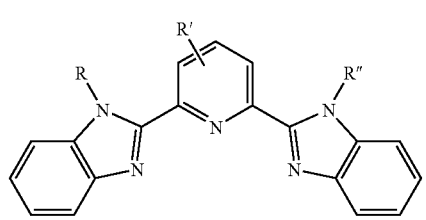

wherein L is a ligand selected from the group of ligands of formula

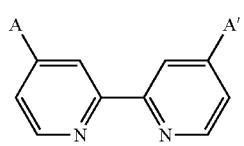

wherein A and A' are anchoring groups selected from COOH, $PO_3H_2$, $PO_4H_2$, $SO_3H_2$, $SO_4H_2$, CONHOH, deprotonated forms thereof and chelating groups with Π conducting character, wherein Z is selected from the group consisting of $H_2O$, Cl, Br, CN, NCO, NCS and NCSe and wherein at least one of substituents R, R', R" comprises a π system in conjugated relationship with the π system of the bidentate, respectively the tridentate structure of formulae (a') to (j), and wherein the other one(s) of substituents R, R', R" is (are) the same or a different substituent including a π system, or is (are) selected from H, OH, R2, $(OR2)_n$, $N(R2)_2$, where R2 is an alkyl of 1-20 carbon atoms and $0<n<5$.

More particularly, the sensitizing dye according to the invention is a complex of formula $$Me\ L1\ L(Z)_2 \quad (I)$$

wherein Me designates Ru, Os or Fe,
wherein L is selected from ligands

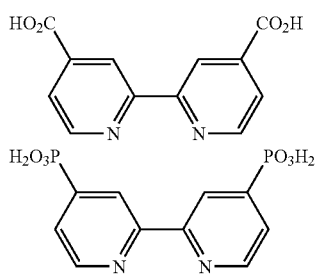

and

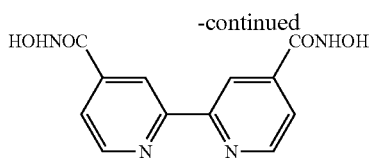

wherein Z is selected from H$_2$O, —Cl, —Br, —I, —CN, —NCO, —NCS and —NCSe.

wherein L1 is a 4,4' disubstituted bipyridine of formula

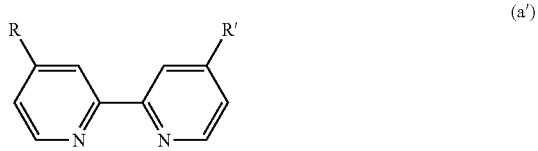

wherein R is a substituent selected from the group of substituents (1), (2) and (3), and R' has the same meaning as above.

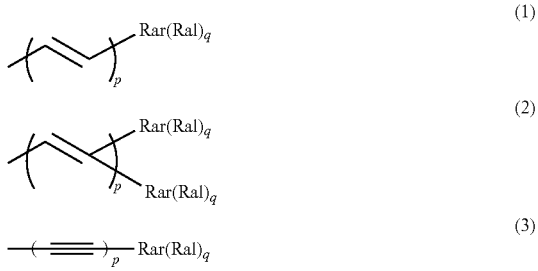

wherein p is an integer from 1 to 4 or is 0
wherein q is an integer from 1 to 4
wherein Rar is a monocyclic or polycyclic aryl from C6 to C22
wherein each —Ral is, independently one from the others, —H, —R1, —(O—R1)$_n$, —NHR1, N(R1)$_2$,

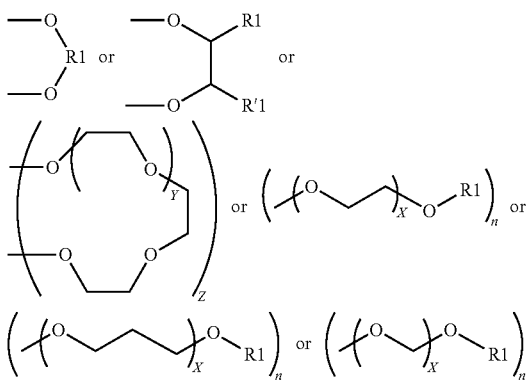

wherein R1, R'1 is an alkyl from 1 to 10 carbon atoms, $20 \geq X \geq 0$, and $5 \geq n \geq 0$, $8 \geq Y \geq 1$, Z=1 or 2.

The use of heteroleptic ruthenium (II) sensitizing dyes may be preferred over the symmetrical ones. Heteroleptic sensitizing dyes can incorporate required properties in one molecule by selecting suitable ligands to enhance the photovoltaic performance.

A preferred family of sensitizers are Ru complexes of formula cis(NCS)$_2$RuLL1, wherein L1 is of formula (a'), wherein R is of formula (1), (2) or (3), wherein p=1, wherein Rar is selected from the group consisting of benzene, naphthalene, wherein q=1 to 4, wherein Ral is OR1 and wherein R1 is an alkyl of 1 to 10 carbon atoms.

Particularly preferred sensitizers are:
cis-dithiocyanato-(2,2'-bipyridyl-4,4'-dicarboxylate) -[4,4'-bis(4-hexyloxystyryl)-2,2' bipyridyl]-Ru(II), hereinafter referred to as K19,
cis-dithiocyanato-(2,2'-bipyridyl-4,4'-dicarboxylate)-[4,4'-bis(4-hexyloxynaphtalene-1-vinyl)-2,2' bipyridyl]-Ru(II), hereinafter referred to as K24,
Cis-dithiocyanato-(2,2'-bipyridyl-4,4'-dicarboxylate) -[4,4'-bis[4-(1,4,7,10-Tetraoxyundecyl)styryl]-2,2'-bipyridine]-Ru(II) hereinafter referred to as K60, and
cis-dithiocyanato-(2,2'-bipyridyl-4,4'-dicarboxylate) -[4,4'-bis(3-methoxystyryl)-2,2' bipyridyl]-Ru(II), hereinafter referred to as Z910.

These new sensitizing dyes have a very high light-harvesting capacity to UV photons. The UV photons can directly excite the wide band-gap metal oxide semiconductor to produce chemically active holes and thus decompose sensitizing dyes and organic electrolyte components or hole-transport materials. After absorbing of UV photons by these new sensitizers, excitons can move rapidly from the donating ligand to the metal center, leaving a hole there and giving an electron to the anchoring ligand, and the electron will be injected to the semiconductor film and realize interfacial charge separation. The strong UV photon absorbing ability makes this type of sensitizer like a "UV filter" while having the advantage of converting the normally unwanted UV photons for dye sensitized solar cells to useful electrons.

These new sensitizing dyes with enhanced light-harvesting capacity are particularly advantageous when used in combination with transparent mesoporous films (no scattering layer), and/or high-viscosity ionic liquid electrolytes, with which thinner mesoporous films are needed to reduce the mass transport problem, said thinner films having a relatively low surface area (larger metal oxide semiconductor particles) for inducing less back electron transfer. Additionally, with this excellent light harvesting property of these sensitizing dyes, less amount of materials are required for efficient devices.

According to a further aspect of the DSSC according to the present invention, an amphiphilic compacting compound is co-adsorbed with the dye on the surface of the semiconductive metal oxide layer forming a mixed monolayer. The molecular structure of said compacting compound comprises at least one anchoring group, a hydrophobic portion and a terminal group.

The anchoring group of the compacting compound, binding to the surface of the semiconductive metal oxide layer, may be the same as the anchoring group of the sensitizing dye or a different one. It may be selected from the group consisting of COOH, PO$_3$H$_2$, PO$_4$H$_2$, SO$_3$H$_2$, SO$_4$H$_2$, CONHOH or deprotonated forms thereof. The anchoring group of the compacting compound may also be a chelating group with π-conducting character, in particular an oxyme, dioxyme, hydroxyquinoline, salicylate or α-keto-enolate group.

The molar ratio of said sensitizing dye to said co-adsorbed compacting compound may be of between 10 and ½, and preferably of between 5 and 1. Depending upon the selection of the dye and the co-adsorbent, i.e. their relative affinity constant for the TiO$_2$ layer, the ratio of dye and co-adsorbent can be varied from 1:10 to 10:1 in their common solvent if they are adsorbed simultaneously, i.e. within the same preparative step. Alternatively, the compacting compound may be adsorbed in a preliminary adsorption step, before the adsorption of the dye, as a pre-treatment, or after the adsorption of the dye, as a post-treatment separate adsorption step.

Since optical density measurements of the mixed monolayer show a decrease in the optical density, if compared to the optical density of an adsorbed monolayer made of a neat dye, it appears that the compacting agent does go onto the surface along with dye molecules, rendering such a monolayer compact. It is thus believed that said sensitizing dye and said compacting compound form a self-assembled compact mixed monolayer on said semiconductive metal oxide layer.

Without being bound by theory, it is believed that the hydrophobic part of the amphiphilic sensitizing dye molecules and the hydrophobic portion of the compacting compound molecules co-adsorbed in the afore-said ratios constitute a closely packed hydrophobic monolayer forming a barrier shielding the surface of the semiconductor metal oxide layer, in particular versus triiodide. It is believed that the triiodide can no more reach the TiO$_2$ surface and that therefore the dark current decreases by decreasing the back electron transfer from the photo injected electrons of TiO$_2$ to triiodide. It is also believed that the hydrophobic portion of the mixed monolayer constitutes a barrier against H$_2$O, hindering water residues to reach the surface of the photoanode. It is further believed that the presence of the co-adsorbing compacting compound contributes in structuring the arrangement of the adsorbed dye molecules.

The terminal group of the compacting compound may be an uncharged group. The terminal group may consist of the free end of an alkyl, alkenyl, alkynyl, alkoxyl or poly-ether chain. The terminal group may consist of a neutral group taking up more space, like a branched alkyl, or a carbon atom substituted by several cycloalkyl or phenyl groups.

Without being bound by theory, it is believed that when the compacting molecules co-adsorbed with the sensitizing dye have a sufficient chain length and if the ends of these chains bear a terminal group (Y) constituted by a bulky neutral hydrophobic group like branched alkyls, these terminal groups have a capping function protecting the dye layer and the anode surface from electrolyte components, among them triiodide, and also from water, the presence of traces of the latter in a DSSC being hardly avoidable.

The terminal group of the compacting compound may be an anionic group. Such terminal group may be selected among the same group as the anchoring groups, that is to say SO$_3^-$, CO$_2^-$, PO$^{2-}_3$, PO$_3$H$^-$, CONHO$^-$. The terminal group of the compacting compound may be a cationic group. Such terminal group may be selected among ammonium, phosphonium, sulfonium, imidazolium, pyrrolidonium and pyridinium groups.

In turn, when the molecules co-adsorbed with the sensitizing dye have a sufficient chain length and if the ends of these chains bear a charged group (Y), these groups surmount the hydrophobic level of the mono-layer and are capable of repelling species present in the electrolyte, thereby preventing once again direct interaction of the species of the electrolyte with parts of the semiconductive metal oxide surface itself.

In view of an outdoor use, exposed to sun at elevated temperatures, the compacting compound is preferably selected so that said self-assembled monolayer is a dense packed monolayer having an order-disorder transition temperature above 80° C.

Preferred compacting compounds are selected among compounds of following formulae (1) to (27)

(1)

(2)

(3)

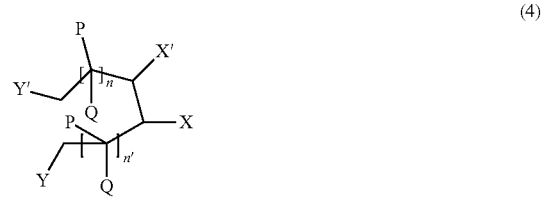

(4)

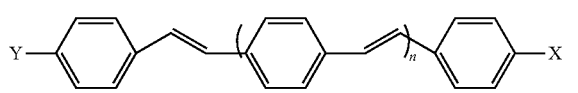

(5)

(6)

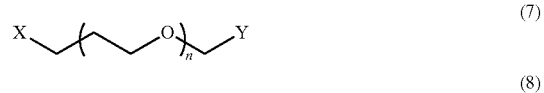

(7)

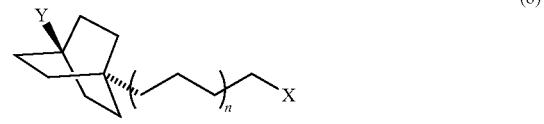

(8)

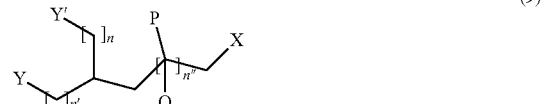

(9)

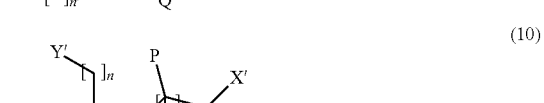

(10)

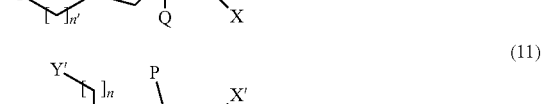

(11)

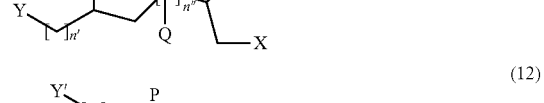

(12)

-continued

(13) 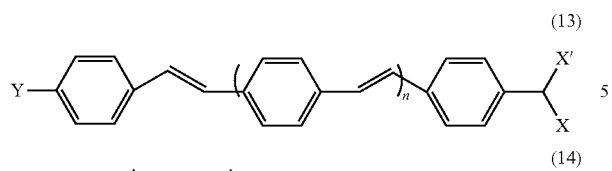

(14) 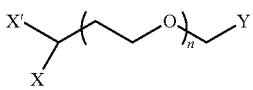

(15) 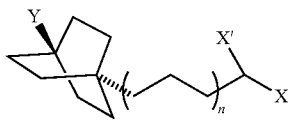

(16) 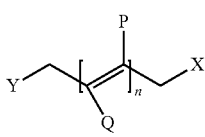

(17) 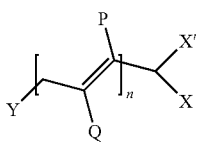

(18) 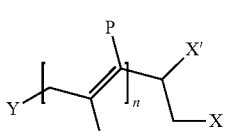

(19) 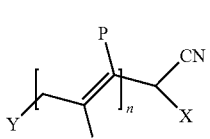

(20) 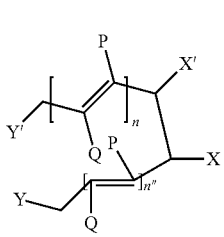

(21) 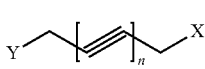

(22) 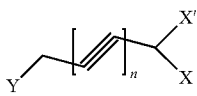

(23) 

(24) 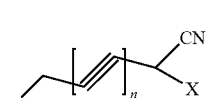

(25) 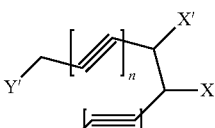

(26) 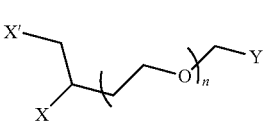

(27) 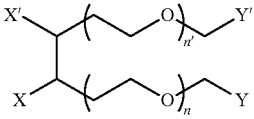

With the proviso that P=Q=H (hydrogen)
or P=H and Q=F (fluoride)
or P=Q=F
that X and X' are, independently one from the other, one of the groups $SO_3^-$, $CO_2^-$, $PO_3^{2-}$, $PO_3H^-$ and $CONHO^-$
that n, n' and n" designate the same or different integers from 1 to 20
that Y and Y' are, independently one from the other, one of the groups $SO_3^-$, $CO_2^-$, $PO_3^{2-}$, $PO_3H^-$ and $CONHO^-$ or a group having one of formulae (101) to (106)

(101) 

(102) 

(103) 

(104) 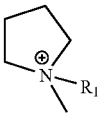

(105) 

(106) 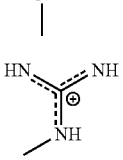

wherein $R_1$, $R_2$, $R_3$ designate independently one from the other H, a phenyl group or an alkyl group of 1 to 20 carbon atoms.

In particular, the compacting compound may be selected from the group consisting of alkyl carboxylic acids, alkyl dicarboxylic acids, alkyl carboxylates, alkyl phosphonic acids, alkyl phosphonates, alkyl diphosphonic acids, alkyl diphosphonates, alkyl sulphonic acids, alkyl sulphonates, alkyl hydroxamic acids, alkyl hydroxamates, wherein alkyl is linear or branched from $C_1$ to $C_{20}$, derivatives of said alkyl hydroxamic acids bearing a terminal group Y of one of formulae (101) to (106) or an anionic terminal group as aforesaid, cyclohexane-carboxylic acid, adamentane acetic acid, adamentane propionic acid and 4-pentylbicyclo(2,2,2)-octane-1-carboxylic acid.

None of the above-cited compacting compounds are electron donating species.

The chain length of the compacting compound, i.e. the length of the hydrophobic portion, is adapted to the dimension of the dye molecule, in particular to the length of substituent R, i.e. $-[H]-(Ral)_q$.

According to another aspect of the DSSC, object of the present invention, the electrolyte of the DSSC may comprise a polar organic solvent having a high boiling point. Boiling points over 100° C. at standard atmospheric pressure are preferred. A suitable compound to be used as organic solvent in the framework of the present invention may be found among nitrites. A preferred nitrile is 3-methoxypropionitrile (MPN). The solvent may be useful on one hand for solubilizing an electrochemically active salt present in the electrolyte, and/or the compound forming the redox couple with an ion of said salt.

In still another aspect of the DSSC according to the present invention, the electrolyte may comprise, instead of an electrochemically active salt which is solid at ambient temperature and shall be dissolved in a solvent, a so-called "room temperature molten salt", an electrochemically active salt having a melting point lower than ambient temperature, or a salt selected so that the mixture formed by this salt and another species of the redox system has a melting point lower than ambient temperature. Then, presence of a solvent may be avoided. The cation of the electrochemically active salt may comprise at least one quaternary nitrogen. The quaternary nitrogen may be comprised in a group selected from imidazolium and triazolium type groups, corresponding to the following general formulae (a) or (b):

(a)

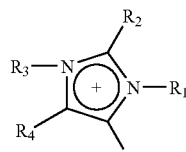

(b)

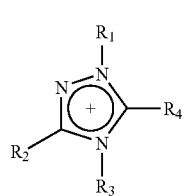

where the groups $R_1$, $R_2$, $R_3$, $R_4$ and $R_5$ are identical or different and are selected from hydrogen and linear or branched alkyl groups, with 1 to 20 carbon atoms, linear or branched alkoxy groups with 1 to 20 atoms of carbon, fluoride substitution derivatives of alkyl groups, alkenyl groups, and combinations of these groups and the corresponding halogenides, or from the alkoxyalkyl and polyether groups.

The cation of the electrochemically active salt may also be an ammonium, a phosphonium or a sulfonium group corresponding to the following general formulae (c), (d) or (e):

(c)

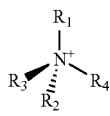

(d)

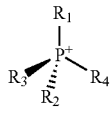

(e)

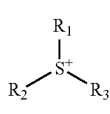

In which groups $R_1$, $R_2$, $R_3$, $R_4$ have the same meanings as above.

The anion of said ionic liquid salt may be selected from halide ions, or a polyhalide ion, or a complex anion containing at least one halide ion, $CF_3SO_3^-$, or $CF_3COO^-$ or $(CF_3SO_2)_3C^-$ or $NO_3^-$ or $PF_6^-$ or $BF_4^-$ or $N(CN)_2^-$ or $NCS^-$ $SeCN^-$ or $ClO_4^-$ or $C(CN)_3^-$ or $R_6SO_3^-$ or $R_6SO_4^-$, where $R_6$ is selected from hydrogen and linear or branched alkyl groups, with 1 to 20 carbon atoms, linear, or branched alkoxy groups with 1 to 20 atoms of carbon.

The redox system of the electrolyte may comprise two salts or more, each having a melting point below ambient temperature, the anions forming a couple of two different electrolytes, for example the iodide/bromide couple.

In a still further aspect of the DSSC, object of the present invention, the electrolyte incorporates a first compound co-operating with either the anion or the cation of the electrochemically active salt, that is to say forming a redox couple with said ion. As a well-known example of such a couple, if the anion of the electrochemically salt is $I^-$, the neutral molecule, respectively element, is iodine.

In still a further aspect of the DSSC, object of the present invention, the electrolyte may incorporate a stabilizing additive in form of a neutral molecule comprising one or more nitrogen atom(s) with a lone electron pair.

Said neutral molecule may be selected from molecules having following formula:

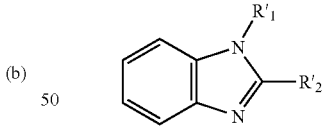

wherein $R'_1$ and $R'_2$ can be H, alkyl, alkoxyl, alkenyl, alkynyl, alkoxy-alkyl, poly-ether, and/or phenyl, independently one from the other, the number of carbon atoms of each substituent ranging from 1 to 20, the substitute being linear or branched.

Preferred compounds are Benzimidazole, 1-methylbenzimidazole, 1-methyl-2-phenyl benzimidazole and 1,2 dimethyl benzimidazole.

The presence of the afore-said neutral additive compound in the electrolyte increases the stability of the DSSC.

BRIEF DESCRIPTION OF THE DRAWINGS

Other particulars and advantages of the DSSC according to the invention, in particular improved performance and stability at high temperature, will appear to those skilled in the art from the description of the following examples in connection with the drawings, which show.

EXAMPLE I

Synthesis of Ligands L1

Figure 1:
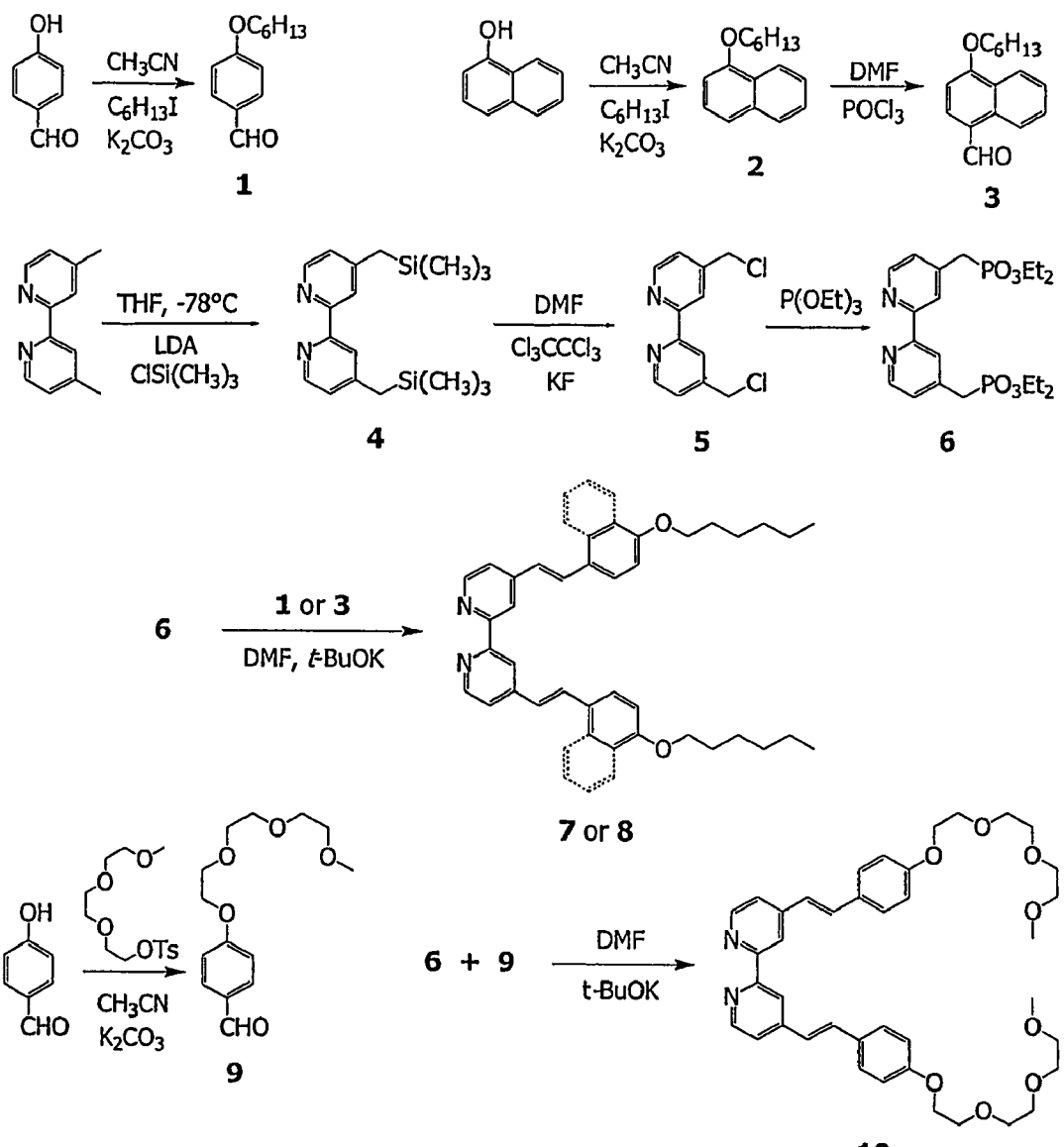
FIG. 1: synthetic route of donating ligands L1.

The synthesis steps are shown in FIG. 1.

1) 4-Hexyloxybenzaldehyde, Intermediate Compound 1

4-formyl-phenol (5 g, 41 mmol), iodohexane (10.5 g, 49 mmol) and K$_2$CO$_3$ (8.5 g, 61 mmol) in acetonitrile (150 ml) were refluxed overnight under N$_2$. After being cooled to room temperature, water (10 ml) was added and acetonitrile was evaporated. Water (150 ml) and Et$_2$O (150 ml) were then added. The ethereal layer was extracted and washed with water (2×100 ml), brine (100 ml), dried over MgSO$_4$, filtered and evaporated to dryness to afford 8.3 g (98%) of compound 1 as a slightly yellow oil after during at 80° C. under vacuum.

$^1$H-NMR (CDCl$_3$, 298K, 200 MHz, δ ppm) 0.94 (t, J=6.5 Hz, 3H), 1.3-1.6 (m, 6H), 1.80 (m, 2H), 4.05 (t, J=6.5 Hz, 2H), 7.00 (d, J=8.7 Hz, 2H), 7.83 (d, J=8.7 Hz, 2H), 9.89 (s, 1H). $^{13}$C-NMR (CDCl$_3$, 298K, 50 MHz, δ ppm) 14.0, 22.5, 25.6, 29.0, 31.5, 68.4, 114.7, 129.7, 131.9, 164.2, 190.7.

2) 1-Hexyloxynaphthalene, Intermediate Compound 2

1-naphthol (5 g, 34.7 mmol), iodohexane (8.82 g, 41.6 mmol) and K$_2$CO$_3$ (7.2 g, 50 mmol) in acetonitrile (150 ml) were refluxed overnight under N$_2$. After being cooled to room temperature, water (10 ml) was added and acetonitrile was evaporated. Water (150 ml) and Et$_2$O (150 ml) were added. The ethereal layer was extracted and washed with water (2×100 ml), brine (100 ml), dried over MgSO$_4$, filtered and evaporated to dryness to afford 7.8 g (98%) of compound 2 as an orange oil after during at 80° C. under vacuum.

$^1$H-NMR (CDCl$_3$, 298K, 200 MHz, δ ppm) 0.99 (t, J=6.5 Hz, 3H), 1.3-1.7 (m, 6H), 1.96 (m, 2H), 4.18 (t, J=6.5 Hz, 2H), 6.84 (dd, J=1.7 and 6.8 Hz, 1H), 7.4-7.6 (m, 4H), 7.84 (m, 1H), 8.35 (m, 1H). $^{13}$C-NMR (CDCl$_3$, 298K, 50 MHz, δ ppm) 14.1, 22.7, 26.0, 29.3, 31.7, 68.1, 104.5, 119.9, 122.1, 125.0, 125.8, 125.9, 126.3, 127.4, 134.5, 154.9.

3) 1-Hexyloxy-4-formylnaphthalene, Intermediate Compound 3

POCl$_3$ (3.22 g, 21 mmol) was dropwise added to a solution of compound 2 (4 g, 17.5 mmol) in anh. DMF (5 ml) at room temperature and under N$_2$. The resulting dark red solution was heated to 100° C. for 3 hours. Concentrated AcONa solution (5 ml) was then added and heating was continued for 2 hours more. After being cooled to room temperature, water (100 ml) was added. The mixture was extracted with Et$_2$O (2×150 ml), the ethereal combined fractions were washed with 10% HCl solution (100 ml), water (100 ml), dried over MgSO$_4$, filtered and evaporated to dryness. Recrystallisation of the brown solid from EtOH afford 2.1 g (47%) of compound 3 as brownish crystals.

$^1$H-NMR (CDCl$_3$, 298K, 200 MHz, δ ppm) 0.95 (t, J=7 Hz, 3H), 1.3-1.7 (m, 6H), 1.98 (m, 2H), 4.24 (t, J=6.4 Hz, 2H), 6.90 (d, J=8 Hz, 1H), 7.58 (t, J=8 Hz, 1H), 7.71 (t, J=8 Hz, 1H), 7.90 (d, J=8 Hz, 1H), 8.37 (d, J=8 Hz, 1H), 9.32 (d, J=8 Hz, 1H), 9.89 (s, 1H). $^{13}$C-NMR (CDCl$_3$, 298K, 50 MHz, δ ppm) 14.0, 22.6, 25.8, 29.0, 31.5, 68.8, 103.5, 122.4, 124.7, 124.8, 125.6, 126.3, 129.4, 131.9, 139.8, 160.4, 192.2.

4) 4,4'-bis[(trimethylsilyl)methyl]-2,2'-bipyridine, Intermediate Compound 4, was Synthesized According to Procedure Published by A. P. Smith, J. J. S. Lamba, and C. L. Fraser (Organic Synthesis, 78, pp. 82-90).

5) 4,4'-bis(chloromethyl)-2,2'-bipyridine, Intermediate Compound 5

A solution composed of compound 4 (2 g, 6.1 mmol), hexachloroethane (5.8 g, 24.3 mmol) and KF (1.42 g, 24.3 mmol) in anhydrous DMF (30 ml) was stirred overnight at room temperature under N$_2$. EtOAc (150 ml) was added. The organic layer was washed with water (5×100 ml), dried over MgSO$_4$ and evaporated to dryness. The resulting solid was dissolved in the minimum volume of hexane and let stand in the freezer for few hours. The resulting white crystalline solid was filtered and washed with small cold portions of hexane to afford 1.4 g (91%) of compound 5 as white crystalline solid.

$^1$H-NMR (CDCl$_3$, 298K, 200 MHz, δ ppm) 4.65 (s, 4H), 7.40 (d, J=5 Hz, 2H), 8.45 (s, 2H), 8.70 (d, J=5 Hz, 2H).

6) 4,4'-bis(diethyl methylphosphonate)-2,2'-bipyridine, Intermediate Compound 6.

Compound 5 (2.6 g, 10.3 mmol) was refluxed overnight under N$_2$ in triethylphosphite (50 ml). Excess P(OEt)$_3$ was evaporated and the resulting brown oil was column chromatographed (Al$_2$O$_3$, CH$_2$Cl$_2$/MeOH: 98/2). The yellow oil thus obtained was dissolved in a mixture of CH$_2$Cl$_2$/hexane (1/50 ml) and let stand in the freezer to afford after filtration 4 g (85%) of compound 6 as a slightly yellow crystalline solid.

$^1$H-NMR (CDCl$_3$, 298K, 200 MHz, δ ppm) 1.27 (t, J=7 Hz, 12H), 3.18 (s, 2H), 3.29 (s, 2H), 4.08 (m, 8H), 7.33 (d, J=5 Hz, 2H), 8.34 (s, 2H), 8.60 (d, J=5 Hz, 2H).

7) Procedure for the Synthesis of 4,4'-bis(4-hexyloxystyryl)-2,2'-bipyridine, Compound 7, and 4,4'-bis(4-hexyloxynaphthalene-1-vinyl)-2,2'-bipyridine, Compound 8.

Solid $^t$BuOK (740 mg, 6.6 mmol) was added to an anh. DMF (50 ml) solution of compound 6 (1 g, 2.2 mmol) and compound 1 or 3 (2.52 g, 5.5 mmol) and the resulting mixture was stirred overnight at room temperature under N$_2$. A copious precipitate appeared after few minutes. DMF was evaporated and the resulting slurry was stirred 30 minutes in MeOH (100 ml). The white precipitate was filtered, washed with small portions of MeOH and dried to afford compound 7 (85%) as a slightly pink solid or compound 8 (78%) as a white solid.

7: $^1$H-NMR (CDCl$_3$, 298K, 200 MHz, δ ppm) 0.93 (t, J=6.3 Hz, 6H), 1.2-1.5 (m, 12H), 1.85 (m, 4H), 4.00 (t, J=6.4 Hz, 4H), 6.93 (d, J=8.7 Hz, 4H), 7.00 (d, J=17 Hz, 2H), 7.38 (d, J=5 Hz, 2H), 7.43 (d, J=17 Hz, 2H), 7.51 (d, J=8.7 Hz, 4H), 8.53 (s, 2H), 8.66 (d, J=5 Hz, 2H). $^{13}$C-NMR (CDCl$_3$, 298K, 50 MHz, δ ppm) 14.0, 22.6, 25.7, 29.2, 31.6, 68.1, 114.8, 118.0, 120.8, 123.8, 128.4, 128.8, 133.0, 146.1, 149.4, 156.5, 159.7.

8: $^1$H-NMR (CDCl$_3$, 298K, 200 MHz, δ ppm)) 0.96 (t, J=7 Hz, 6H), 1.3-1.7 (m, 12H), 1.98 (m, 4H), 4.21 (t, J=6.4 Hz, 4H), 6.88 (d, J=8 Hz, 2H), 7.13 (d, J=16 Hz, 2H), 7.50-7.67 (m, 6H), 7.75 (d, J=8 Hz, 2H), 8.20 (d, J=16 Hz, 2H), 8.22-8.27 (m, 2H), 8.36-8.41 (m, 2H), 8.64 (s, 2H), 8.73 (d, J=5 Hz, 2H). $^{13}$C-NMR (CDCl$_3$, 298K, 50 MHz, δ ppm) 14.4, 22.6, 25.9, 29.2, 31.6, 68.3, 104.6, 118.4, 120.9, 122.7, 123.3, 124.8, 125.2, 125.7, 126.1, 126.9, 127.0, 130.4, 132.3, 146.3, 149.5, 155.7, 156.6.

10) 4,4'-bis[4-(1,4,7,10-Tetraoxyundecyl)styryl]-2,2'-bipyridine.

3,6,9-Trioxydecyl 4-toluenesulfonate and 4-(1,4,7,10-Tetraoxyundecyl)benzaldehyde were synthesized according to reference C. Lottner, K.-C. Bart, G. Bernhardt, H. Brunner *J. Med. Chem.* 2002, 45, 2079-2089).

Solid tBuOK (1.5 g, 13.4 mmol) was added to a solution of 4,4'-bis(diethylmethylphosphonate)-2,2'-bipyridine (1.5 g, 3.3 mmol) and 4-(1,4,7,10-Tetraoxyundecyl)benzaldehyde (2.1 g, 7.8 mmol) in anhydrous DMF (80 ml). The resulting mixture was stirred overnight at room temperature under nitrogen. After evaporation of DMF, water (100 ml) was added and extracted with CH$_2$Cl$_2$ (3×150 ml). The combined organic fractions were washed with water (100 ml), brine (100 ml), dried over MgSO$_4$, filtered and evaporated to dryness. The resulting residue was then dissolved in the minimum volume of CH$_2$Cl$_2$ and precipitated by addition of Et$_2$O with rapid stirring. The solid was filtered, washed with Et$_2$O and dried to afford 1.5 g (66%) of the titled compound as a slightly beige solid.

$^1$H NMR (200 MHz, 25° C., CDCl$_3$) δ 3.39 (s, 6H), 3.5-3.7 (m, 16H), 3.88 (t, J=4.5 Hz, 4H), 4.18 (t, J=4.5 Hz, 4H), 6.94 (d, J=8 Hz, 4H), 7.00 (d, J=16 Hz, 2H), 7.4-7.5 (m, 8H), 8.52 (s, 2H), 8.65 (d, J=5 Hz, 2H). $^{13}$C NMR (50 MHz, 25° C., CDCl$_3$) δ 59.0, 67.5, 69.7, 70.6, 70.7, 70.8, 71.9, 114.9, 118.0, 120.8, 124.0, 128.4, 129.2, 132.8, 146.1, 149.4, 156.5, 159.3.

Those skilled in the art will observe that if the symmetric starting compound of step 4, e.g. 4,4'-bis(methyl) -2,2'-bipyridine is replaced by an asymmetric starting compound, e.g. 4-methyl-2,2'-bipyridine, an asymmetric compound L1, e.g. 4-(4-hexyloxystyryl)-2,2' bipyridine will be synthesized.

EXAMPLE II

Synthesis of Z910

The synthesis of Z910 was performed according to a one pot synthesis method reported in Nat. Mater (2003) 2, 402. [RuCl$_2$(p-cymene)]$_2$ (0.15 g, 0.245 mmol) was dissolved in DMF (50 ml) and to this solution dmsbpy (0.206 g, 0.49 mmol) was added. The reaction mixture was heated to 60° C. under nitrogen for 4 h with constant stirring. To this reaction flask H$_2$dcbpy (0.12 g, 0.49 mmol) was added and refluxed for 4 h. Finally, excess of NH$_4$NCS (13 mmol) was added to the reaction mixture and continued the reflux for another 4 h. The reaction mixture was cooled down to room temperature and the solvent was removed by using rotary-evaporator under vacuum. Water was added to the flask and the insoluble solid was collected on a sintered glass crucible by suction filtration. The crude was dissolved in a basic methanol solution and purified by passing through a Sephadex LH-20 column with methanol as an eluent. After collecting main band and evaporating the solvent, the resultant solid was redissolved in water. Lowering the pH to 3.1 by titration with dilute nitric acid produced Z910 as a precipitate. The final product was washed thoroughly with water and dried under vacuum. $^1$H NMR (δ$_H$/ppm in CD$_3$OD+ NaOD) 9.4 (d, 1H), 9.2 (d, 1H), 8.9 (s, 1H), 8.8 (s, 1H), 8.3 (s, 1H), 8.15 (s, 1H), 7.9 (d, 1H), 7.80 (d, 1H), 7.7 to 6.9 (m, 16H), 4.1 (s, 3H), 4.0 (s, 3H). Anal. Calc. for RuC$_{42}$H$_{34}$N$_6$O$_7$S$_2$: C, 56.0; H, 3.78; N, 9.34%. Found: C, 55.22; H, 3.97; N, 9.39%.

Figure 13:
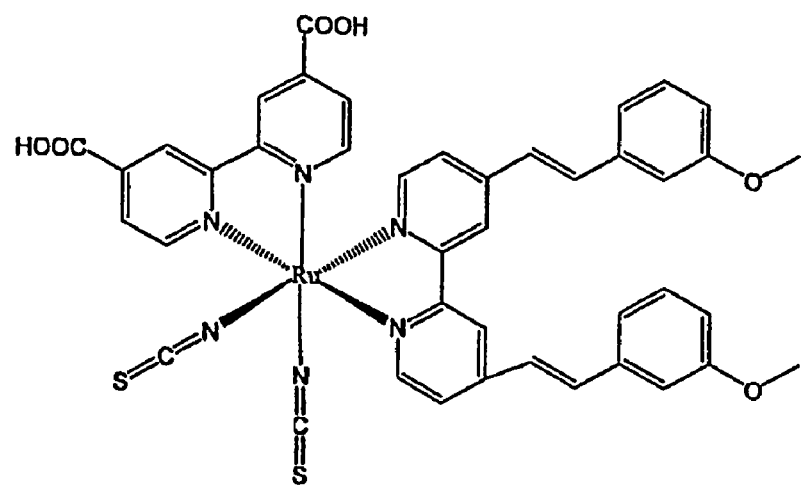
FIG. 13: the molecular structures of K 60 and Z910.
Figure 13:
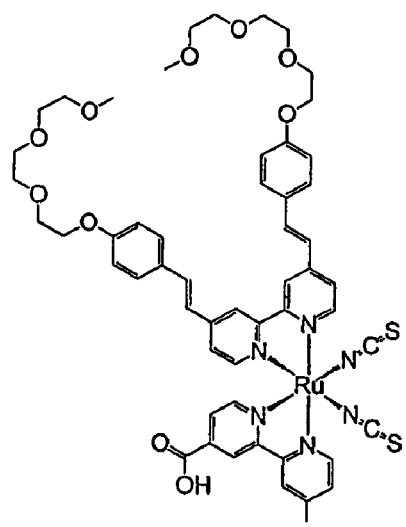

The molecular structure of Z910 is given in FIG. 13.

Figure 3:
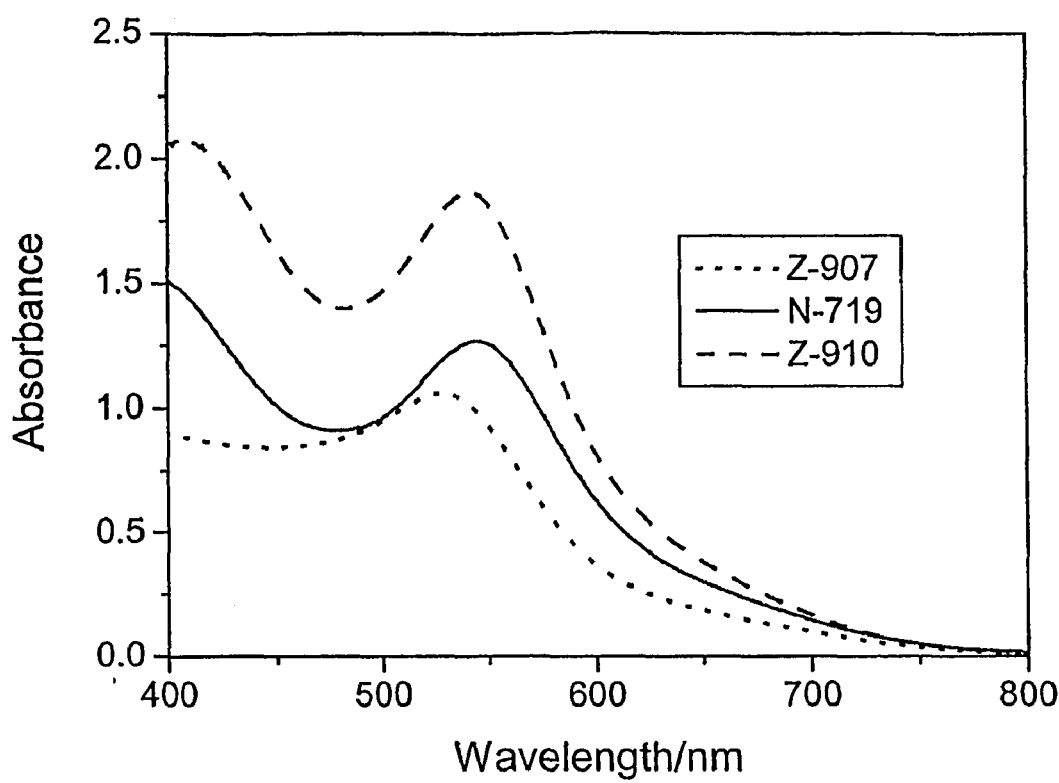
FIG. 3: absorption spectra of Z910, N-719, and Z-907 anchored on a 8 μm thickness transparent nanocrystalline TiO$_2$ film.

FIG. 3 compares the electronic absorption spectra of 8 [m mesoporous TiO$_2$ films grafted respectively with Z907, N719 and Z910 dyes.

By extending the π-conjugated system of the ligand, the metal-to-ligand charge transfer (MLCT) transitions are red shifted with higher molar extinction coefficient. In addition to the increase in the optical density of MLCT transitions there is a huge increase in the optical density of ligand to ligand charge transitions in the UV regions. These UV transitions can serve as UV filters in DSSCs

EXAMPLE III

Figure 2:
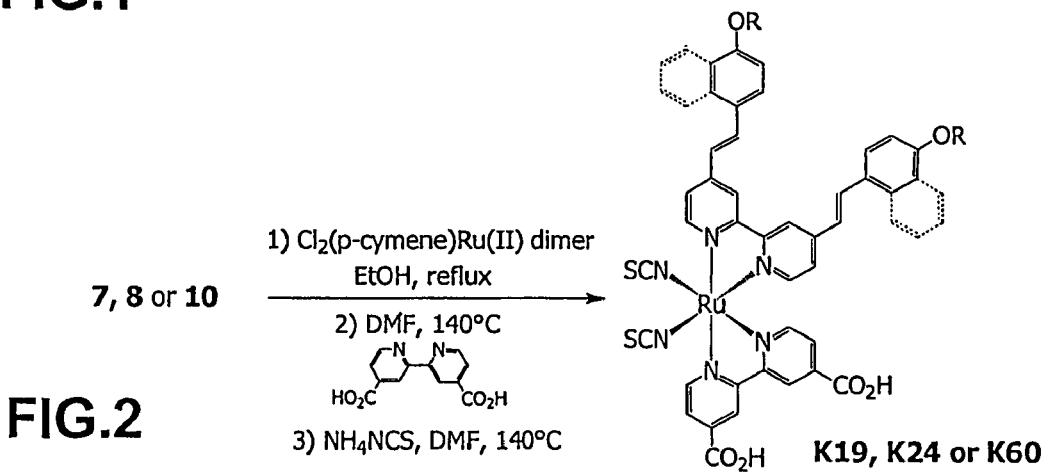
FIG. 2: synthetic route of RuLL1(NCS)$_2$.

The Synthesis Steps of K19 or K24 or K60 are Shown in FIG. 2.

Synthesis of Dye K19 Ru(LL1) (NCS)$_2$

Compound 7 (200 mg, 0.36 mmol) and dichloro(p-cymene)ruthenium(II) dimer (109 mg, 0.18 mmol) were refluxed in argon degased EtOH (50 ml) for 4 hours under argon. The orange-brown solution was evaporated to dryness to afford quantitatively the intermediate complex RuL(p-cymene)Cl$_2$ as a brown solid. This complex and 4,4'-dicarboxy-2,2'-bipyridine (88 mg, 0.36 mmol) were heated to 140° C. in degased anh. DMF for 4 hours under argon and in the dark. To the resulting dark green solution was added solid NH$_4$NCS (411 mg, 5.4 mmol) and the mixture was allowed to heat 4 hours more at 140° C. under argon and in the dark. DMF was evaporated and water (200 ml) was added. The formed purple solid was filtered off, washed with water, Et$_2$O, and purified on LH-20 sephadex to afford complex K$_{19}$. $^1$H NMR (δ$_H$/ppm in CD$_3$OD+ NaOD) 9.4 (d, 1H), 9.2 (d, 1H), 8.9 (s, 1H), 8.8 (s, 1H), 8.3 (s, 1H), 8.15 (s, 1H), 8.0 (d, 1H), 7.80 (d, 1H), 7.7 to 6.9 (m, 16H), 4.1 (s, 3H), 1.8 (t, 2H), 1.6 to 1.4 (m, 8H), 1.0 (t, 3H). The molecular structure of Ru(d-cbpy) (dmsbpy) (NCS)$_2$ (where dcbpy is 4,4'-dicarboxylic acid-2,2'-bipyridine) referred to K19 is shown in FIG. 2.

EXAMPLE IV

Synthesis of Dye K24 Ru (LL1) (NCS)$_2$

Compound 8 (300 mg, 0.45 mmol) and dichloro(p-cymene)ruthenium(II) dimer (139 mg, 0.227 mmol) were refluxed in argon degased EtOH (50 ml) for 4 hours under argon. The orange-brown solution was evaporated to dryness to afford quantitatively the intermediate complex RuL(p-cymene)Cl$_2$ as a brown solid. This complex and 4,4'-dicarboxy-2,2'-bipyridine (111 mg, 0.45 mmol) were heated to 140° C. in degased anh. DMF for 4 hours under argon and in the dark. To the resulting dark green solution was added solid NH$_4$NCS (520 mg, 6.8 mmol) and the mixture was allowed to heat 4 hours more at 140° C. under argon and in the dark.

DMF was evaporated and water (200 ml) was added. The formed purple solid was filtered off, washed with water, $Et_2O$, and purified on LH-20 sephadex to afford complexes K24.

EXAMPLE V

Synthesis of Dye K 60: Ru(LL') $(NCS)_2$

Compound 10 (850 mg, 1.24 mmol) and dichloro(p-cymene)ruthenium(II) dimer (380 mg, 6.2 mmol) were refluxed in argon degased EtOH (50 ml) for 4 hours under argon. The orange-brown solution was evaporated to dryness to afford quantitatively the intermediate complex RuL(p-cymene)$Cl_2$ as a brown solid. This complex and 4,4'-dicarboxy-2,2'-bipyridine (303 mg, 1.24 mmol) were heated to 140° C. in degased anh. DMF for 4 hours under argon and in the dark. To the resulting dark green solution was added excess solid $NH_4NCS$ (1.5 g) and the mixture was allowed to heat 4 hours more at 140° C. under argon and in the dark. DMF was evaporated and water (200 ml) was added. The formed purple solid was filtered off, washed with water, $Et_2O$, and purified on LH-20 sephadex to afford complex K 60 as purple solid. The molecular structure of Ru (dcbpy) (4,4'-bis[4-(1,4,7,10-Tetraoxyundecyl)styryl]-2,2'-bipyridine $(NCS)_2$ (where dcbpy is 4,4'-dicarboxylic acid-2,2'-bipyridine) referred to K 60 is shown in FIG. 13.

EXAMPLE VI

Fabrication and Photovoltaic Performance of Z910 Sensitized Solar Cells

A screen-printed double layer of $TiO_2$ particles was used as photoanode. A 10 μm thick film of 20 nm sized $TiO_2$ particles was first printed on the fluorine-doped $SnO_2$ conducting glass electrode and further coated by 4 μm thick second layer of 400 nm sized light scattering anatase particles. Fabrication procedure for the nanocrystalline $TiO_2$ photoanodes and the assembly as well as photoelectrochemical characterization of complete, hot-melt sealed cells has been described by P. Wang et al. (J. Phys. Chem. B, 2003, 107, 14336-14341). The electrolyte used for device A contained 0.6 M 1-propyl-3-methylimidazolium iodide (PMII), 30 mM M $I_2$, 0.13 M guanidinium thiocyanate, and 0.5 M 4-tert-butylpyridine in the 1:1 volume mixture of acetonitrile and valeronitrile. The $TiO_2$ electrodes were immersed at room temperature for 12 h into a solution containing 300 μM Z910 and 300 μM chenodeoxycholic acid in acetonitrile and tert-butanol (volume ratio: 1:1). For stability tests, the electrolyte was composed of 0.6 M PMII, 0.1 M $I_2$, and 0.5 M N-methylbenzimidazole in 3-methoxypropionitrile and the corresponding device with the Z910 dye alone is denoted as device B.

Figure 4:
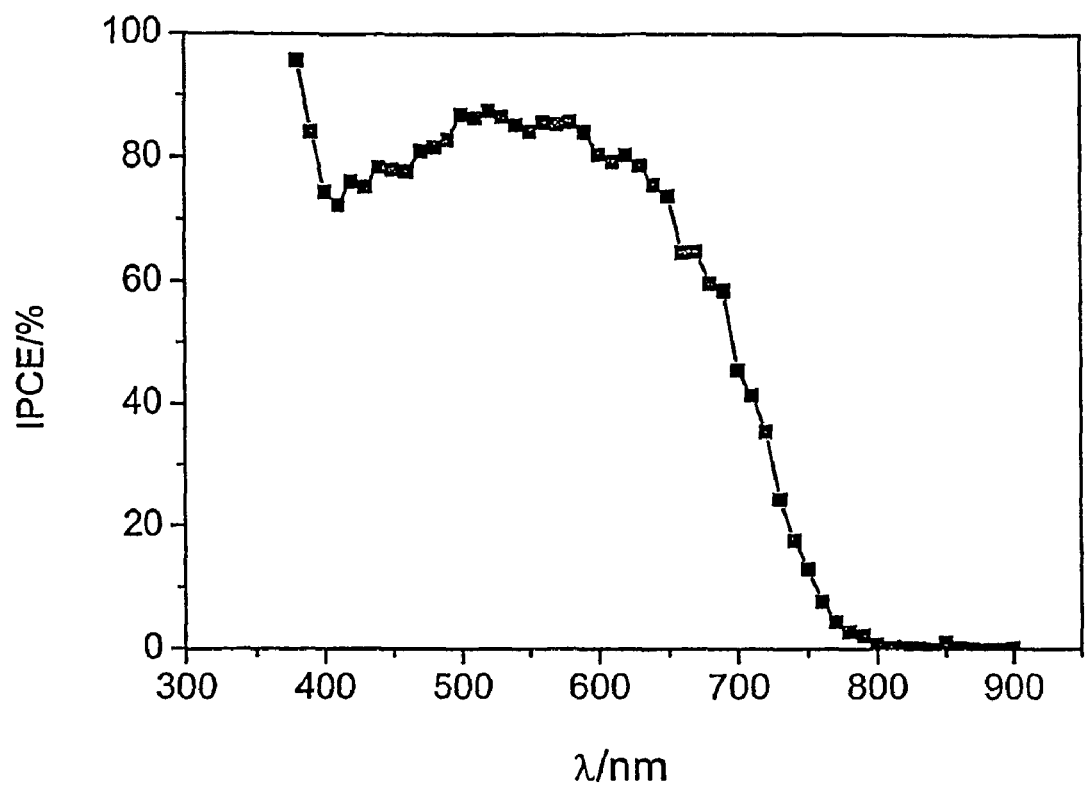
FIG. 4: photocurrent action spectrum of device A sensitised with Z910 dye.
Figure 5:
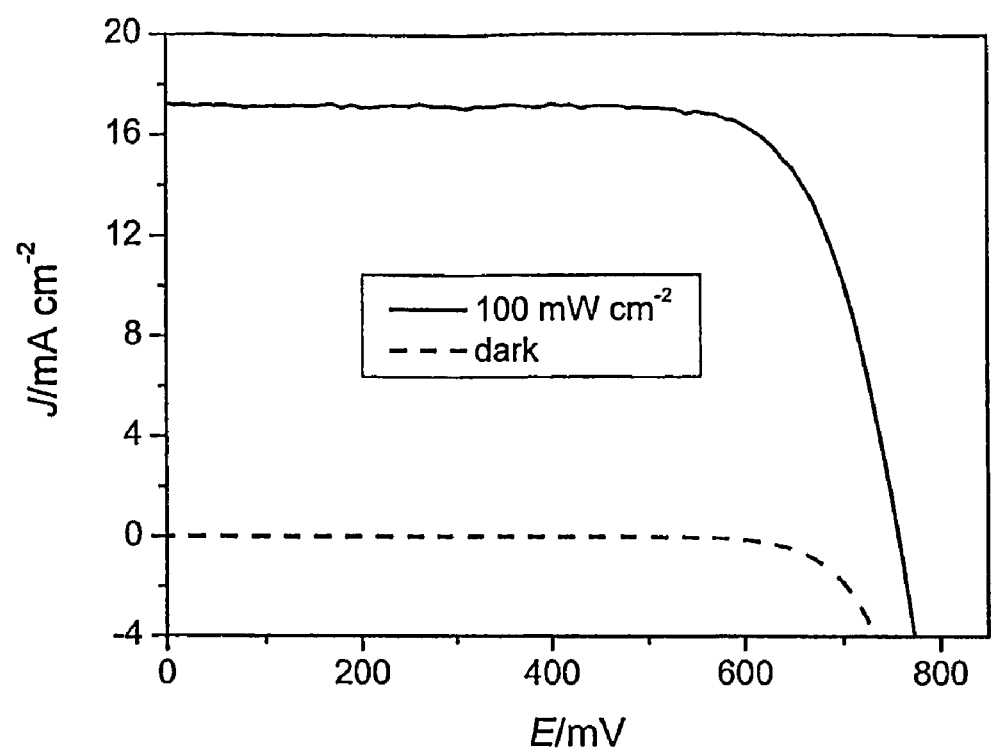
FIG. 5: current density-voltage characteristics of devices A with Z910 dye under AM 1.5 sunlight (100 mW cm$^{-2}$) illumination and in the dark. Cell active area: 0.158 cm$^2$. Outside of the active area is completely masked with black plastic to avoid the diffusive light.

The photocurrent action spectrum of device A with Z910 as sensitizer is shown in FIG. 4. The incident photon to current conversion efficiency (IPCE) exceeds 80% in a spectral range from 470 to 620 nm, reaching its maximum of 87% at 520 nm. Considering the light absorption and scattering loss by the conducting glass, the maximum efficiency for absorbed photon to current conversion efficiency is practically unity over this spectral range. From the overlap integral of this curve with the standard global AM 1.5 solar emission spectrum, a short-circuit photocurrent density ($J_{sc}$) of 17.2 mA $cm^{-2}$ is calculated, which is in excellent agreement with the measured photocurrent. As shown in FIG. 5, its short-circuit photocurrent density ($J_{sc}$), open-circuit photovoltage ($V_{oc}$), and fill factor (ff) of device A with Z910 dye under AM 1.5 full sunlight are 17.2 mA $cm^{-2}$, 777 mV, and 0.764, respectively, yielding an overall conversion efficiency (η) of 10.2%. At various lower incident light intensities, overall power conversion efficiencies are also over 10.2%. With the double layer film (total thickness of 14 μm) and electrolyte used here, the power conversion efficiencies of N-719 and Z-907 dyes are 7% less efficient than Z910.

Figure 6:
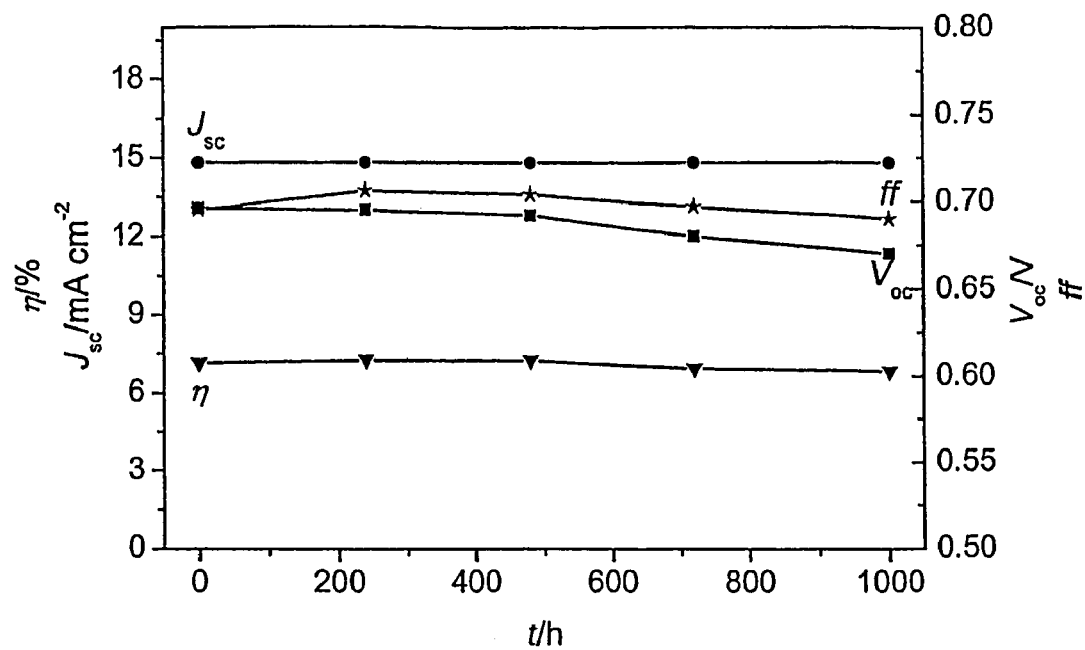
FIG. 6: detailed photovoltaic parameters of devices B with Z910 dye during successive one sun visible-light soaking at 55° C.

The above-mentioned 3-methoxypropionitrile based electrolyte was used for the stability test of sensitizer Z910 under moderate thermal stress and visible light soaking. The advantage of using 3-methoxypropionitrile lies in its high boiling point, low volatility, non-toxicity and good photochemical stability, making it viable for practical application. Photovoltaic parameters (Jsc, Voc, ff, and η) of device B are 14.8 mA $cm^{-2}$, 696 mV, 0.695, and 7.2%, respectively. The cells covered with a 50 μm thick of polyester film (Preservation Equipment Ltd, UK) as a UV cut-off filter (up to 400 nm) were irradiated at open circuit under a Suntest CPS plus lamp (ATLAS GmbH, 100 mW $cm^{-2}$, 55° C.). As shown in FIG. 6, all parameters of the device are rather stable during 1000 h accelerating tests. It should be noted that under this condition the sensitizer showed similar stability but higher efficiency compared with Z-907 dye.

EXAMPLE VII

Fabrication and Photovoltaic Performance of K19 Sensitized Solar Cells with a Organic Solvent Based Electrolyte A screen-printed double layer of $TiO_2$ particles was used as photoanode. A 10 μm thick film of 20 nm sized $TiO_2$ particles was first printed on the fluorine-doped $SnO_2$ conducting glass electrode and further coated by 4 μm thick second layer of 400 nm sized light scattering anatase particles. Fabrication procedure for the nanocrystalline $TiO_2$ photoanodes and the assembly as well as photoelectrochemical characterization of complete, hot-melt sealed cells C has been described above. The electrolyte used for device C contained 0.6 M 1,2-dimethyl-3-propylimidazolium iodide (DMPII), 0.1 mM M $I_2$, and 0.5 μM N-methylbenzimidazole in 3-methoxypropionitrile. The $TiO_2$ electrodes were immersed at room temperature for 12 h into a solution containing 300 μM K19 in the mixture of acetonitrile and tert-butanol (volume ratio: 1:1).

Figure 7:
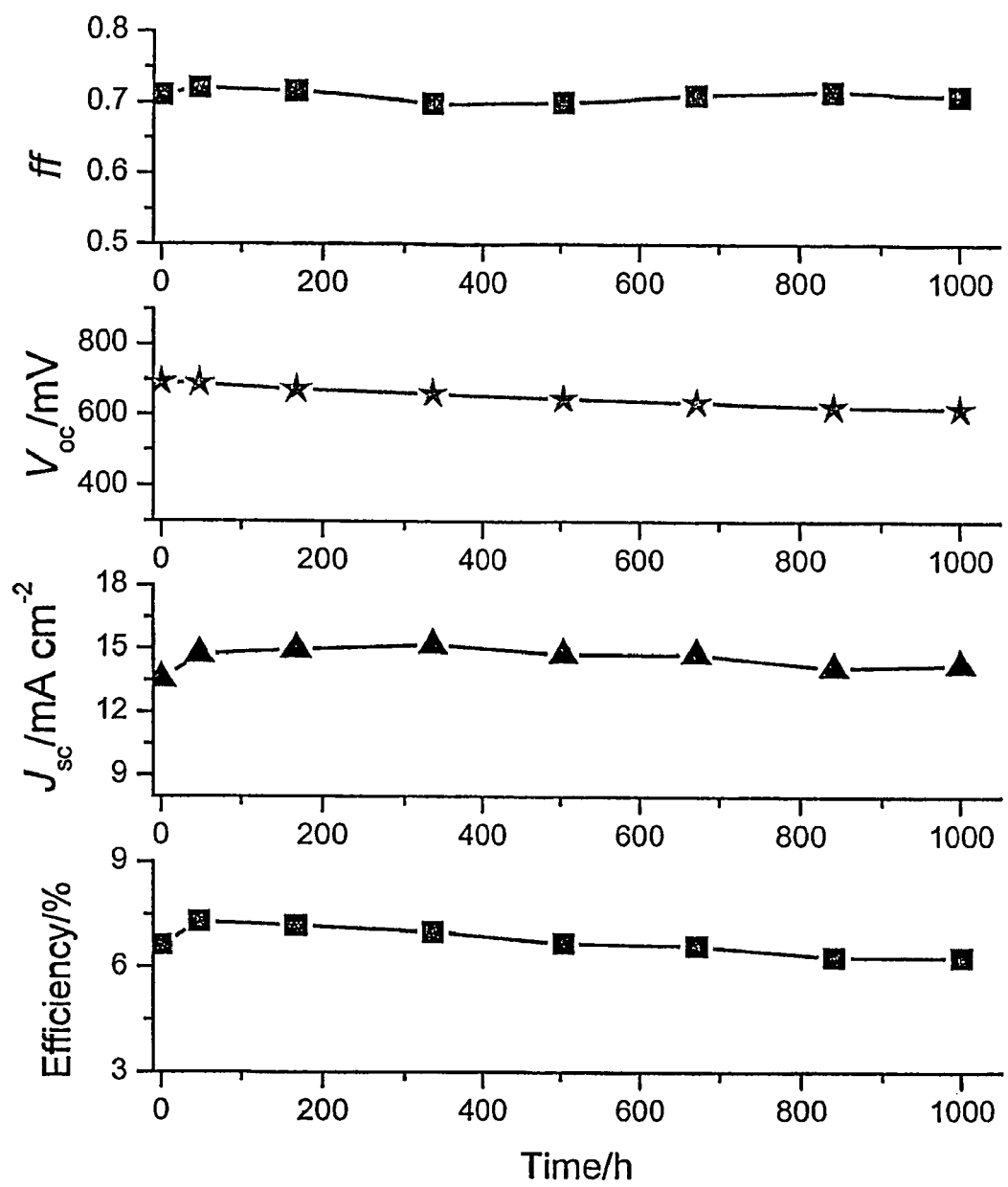
FIG. 7: detailed photovoltaic parameters of devices C with K19 dye at 80° C.
Figure 8:
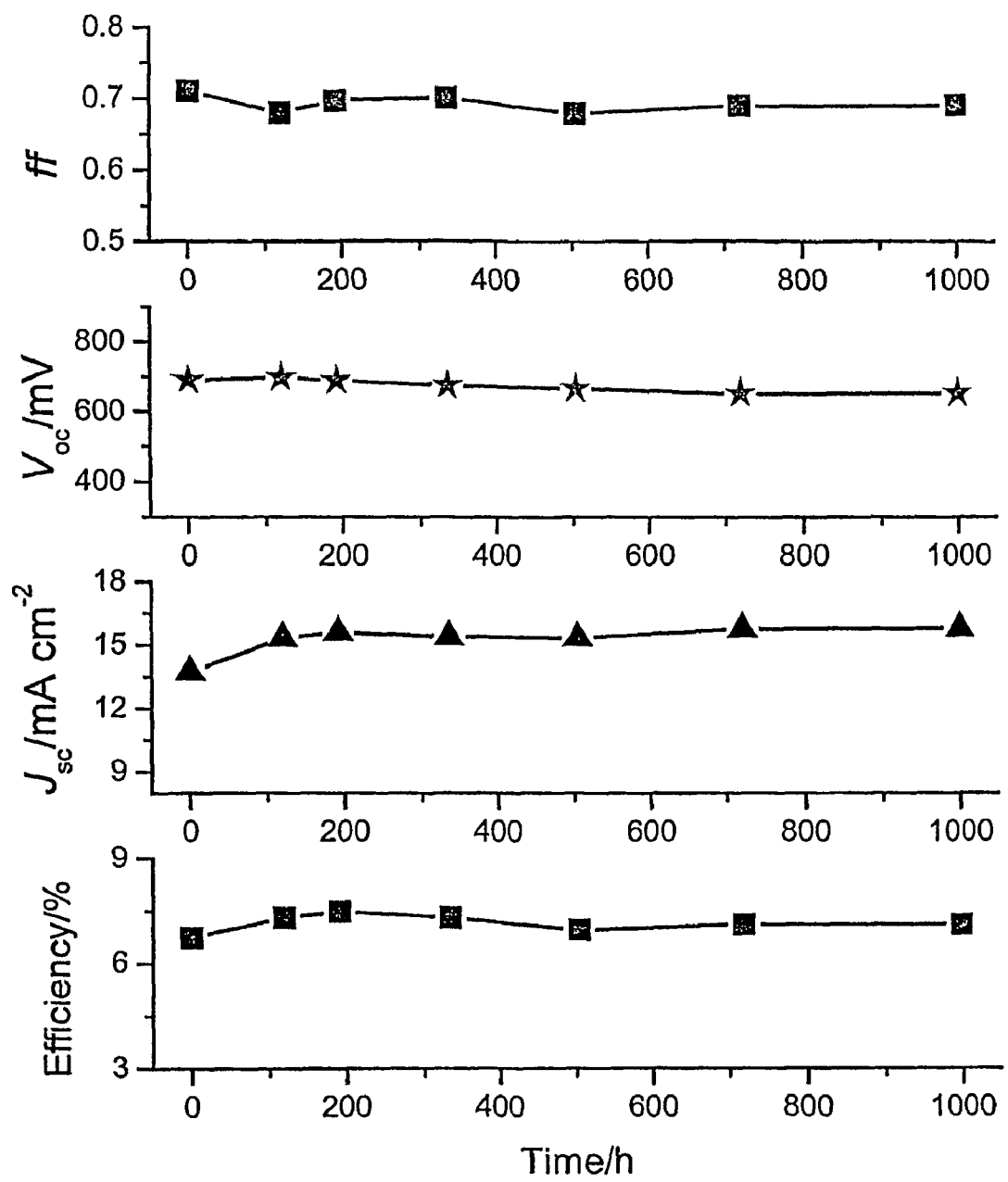
FIG. 8: detailed photovoltaic parameters of devices C with K19 dye during successive one sun visible-light soaking at 55° C.

FIG. 7 shows the evolution of photovoltaic parameters of device C at 80° C. in the dark. FIG. 8 shows the evolution of photovoltaic parameters of device C covered with a UV filter at 55-60° C. under AM 1.5 sunlight (100 mW/$cm^2$).

EXAMPLE VIII

Fabrication and Photovoltaic Performance of K19 Sensitized Solar Cells with a Organic Solvent Based Electrolyte A screen-printed double layer of $TiO_2$ particles was used as photoanode. A 10 μm thick film of 20 nm sized $TiO_2$ particles was first printed on the fluorine-doped $SnO_2$ conducting glass electrode and further coated by 4 μm thick second layer of 400 nm sized light scattering anatase particles. Fabrication procedure for the nanocrystalline $TiO_2$ photoanodes and the assembly as well as photoelectrochemical characterization of complete, hot-melt sealed cells has been described as above. The electrolyte used for device D contained 0.2 M $I_2$, and 0.5 M N-methylbenzimidazole in the 65/35 volume mixture of 1-propyl-3-methylimidazolium iodide (PMII) and 1-ethyl-2-methylimidazolium tricyanomethide [EMIC$(CN)_3$]. The $TiO_2$ electrodes were immersed at room temperature for 12 h into a solution containing 300 μM K$_{19}$ in the mixture of acetonitrile and tert-butanol (volume ratio: 1:1). Table 1 gives the detailed photovoltaic paprameters of device D under illumination of different light intensities.

TABLE 1

Detailed photovoltaic parameters of device D.

| P$_{in}$/mW cm$^{-2}$ | J$_{sc}$/mA cm$^{-2}$ | V$_{oc}$/mV | P$_{max}$/mW cm$^{-2}$ | ff | η/% |
|---|---|---|---|---|---|
| 9.45 | 1.42 | 634 | 0.7 | 0.78 | 7.4 |
| 51.7 | 7.31 | 682 | 3.75 | 0.77 | 7.2 |
| 99.9 | 13.0 | 700 | 6.7 | 0.74 | 6.7 |

The spectral distribution of the lamp simulates air mass 1.5 solar light. Incident power intensity: P$_{in}$; Short-circuit photocurrent density: J$_{sc}$; Open-circuit photovoltage: V$_{oc}$; Maximum electricity output power density: P$_{max}$; Fill factor: ff=P$_{max}$/P$_{in}$; Total power conversion efficiency: η. Cell active area: 0.158 cm$^2$.

EXAMPLE IX

Fabrication and Photovoltaic Performance of Cells with a TiO$_2$ Film Cografted with K19 Dye and 1-decylphosphonic Acid Coadsorbent A screen-printed double layer of TiO$_2$ particles was used as photoanode. A 10 μm thick film of 20 nm sized TiO$_2$ particles was first printed on the fluorine-doped SnO$_2$ conducting glass electrode and further coated by 4 μm thick second layer of 400 nm sized light scattering anatase particles. Fabrication procedure for the nanocrystalline TiO$_2$ photoanodes and the assembly as well as photoelectrochemical characterization of complete, hot-melt sealed cells has been described above. The electrolyte used for device E contained 0.6 M 1,2-dimethyl-3-propylimidazolium iodide (DMPII), 0.1 mM M I$_2$, and 0.5 M N-methylbenzimidazole in 3-methoxypropionitrile. The TiO$_2$ electrodes were immersed at room temperature for 12 h into a solution containing 300 μM K$_{19}$ dye and 75 μM 1-decylphosphonic acid coadsorbent in the mixture of acetonitrile and tert-butanol (volume ratio: 1:1).

Figure 9:
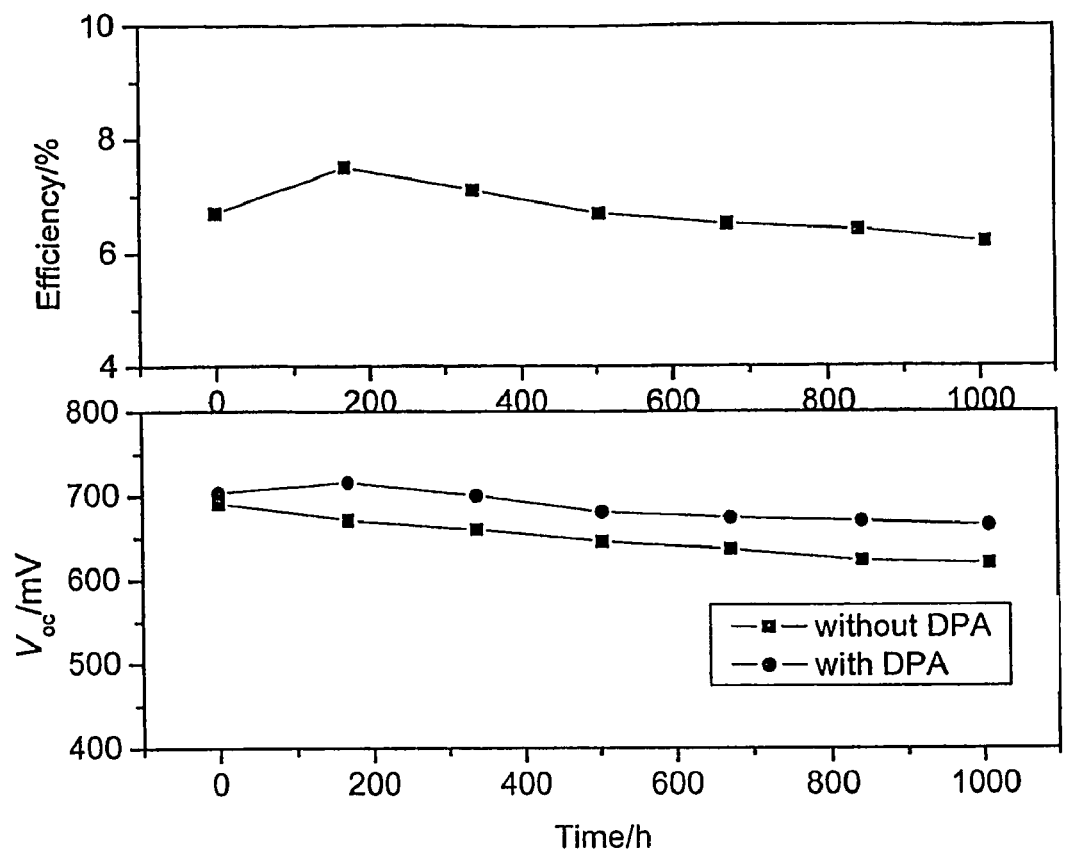
FIG. 9: detailed photovoltaic parameters of devices E with K19 dye and 1-decylphosphonic acid as coadsorbent at 80° C.
Figure 10:
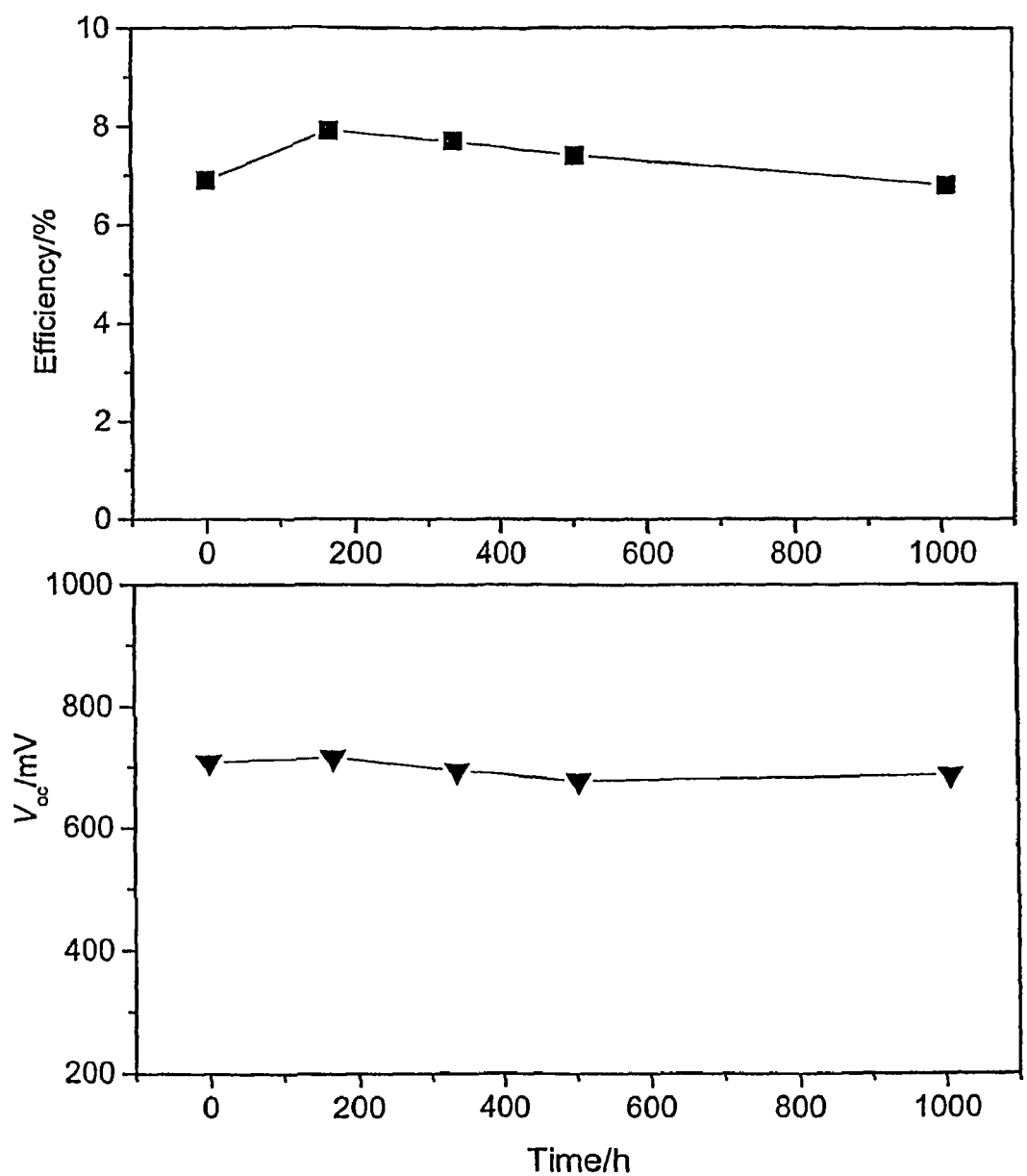
FIG. 10: detailed photovoltaic parameters of devices E with K19 dye and 1-decylphosphonic acid as coadsorbent during successive one sun visible-light soaking at 55° C.
Figure 11:
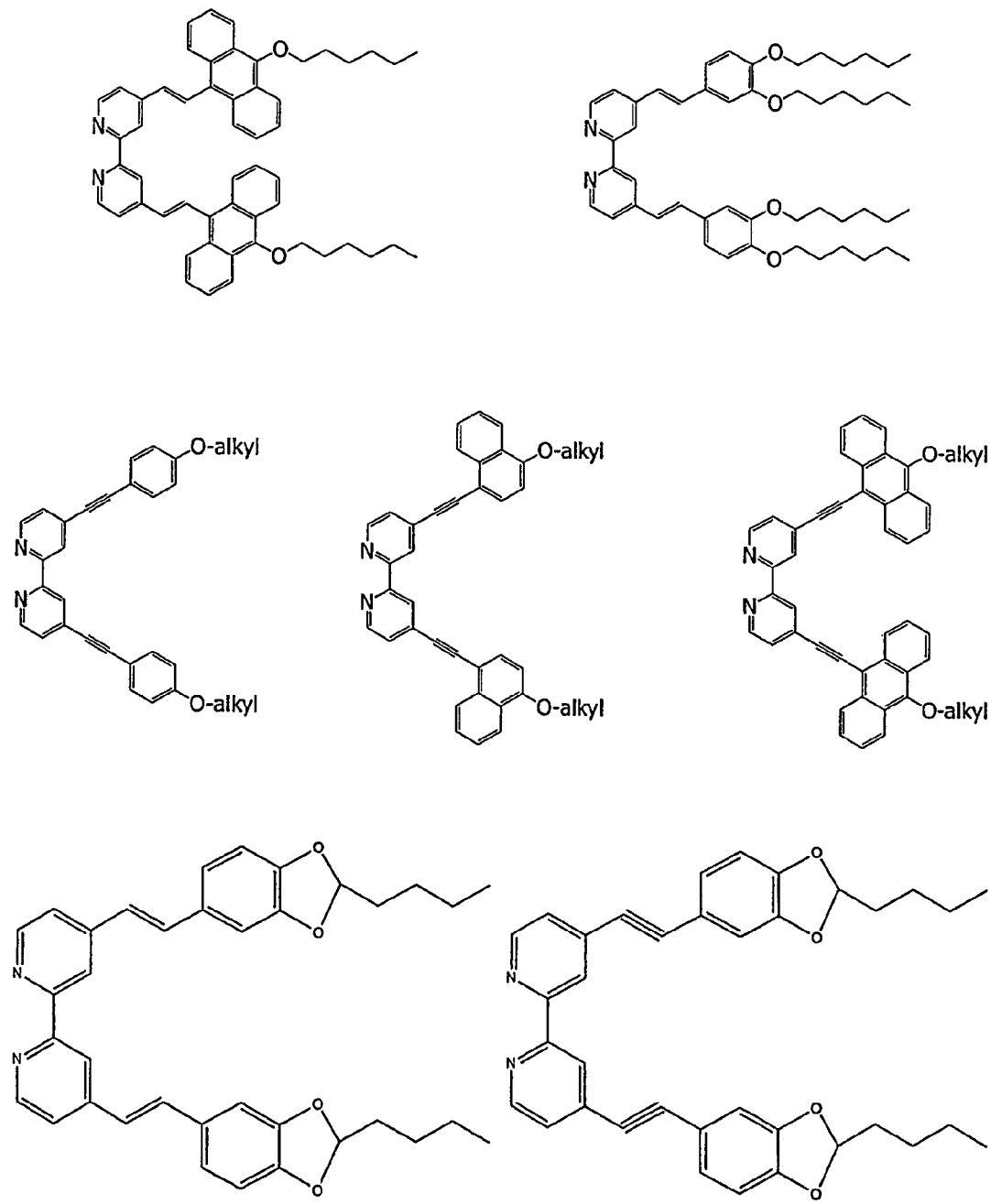
FIGS. 11 and 12: the molecular structures of examples of ligands L1.
Figure 12:
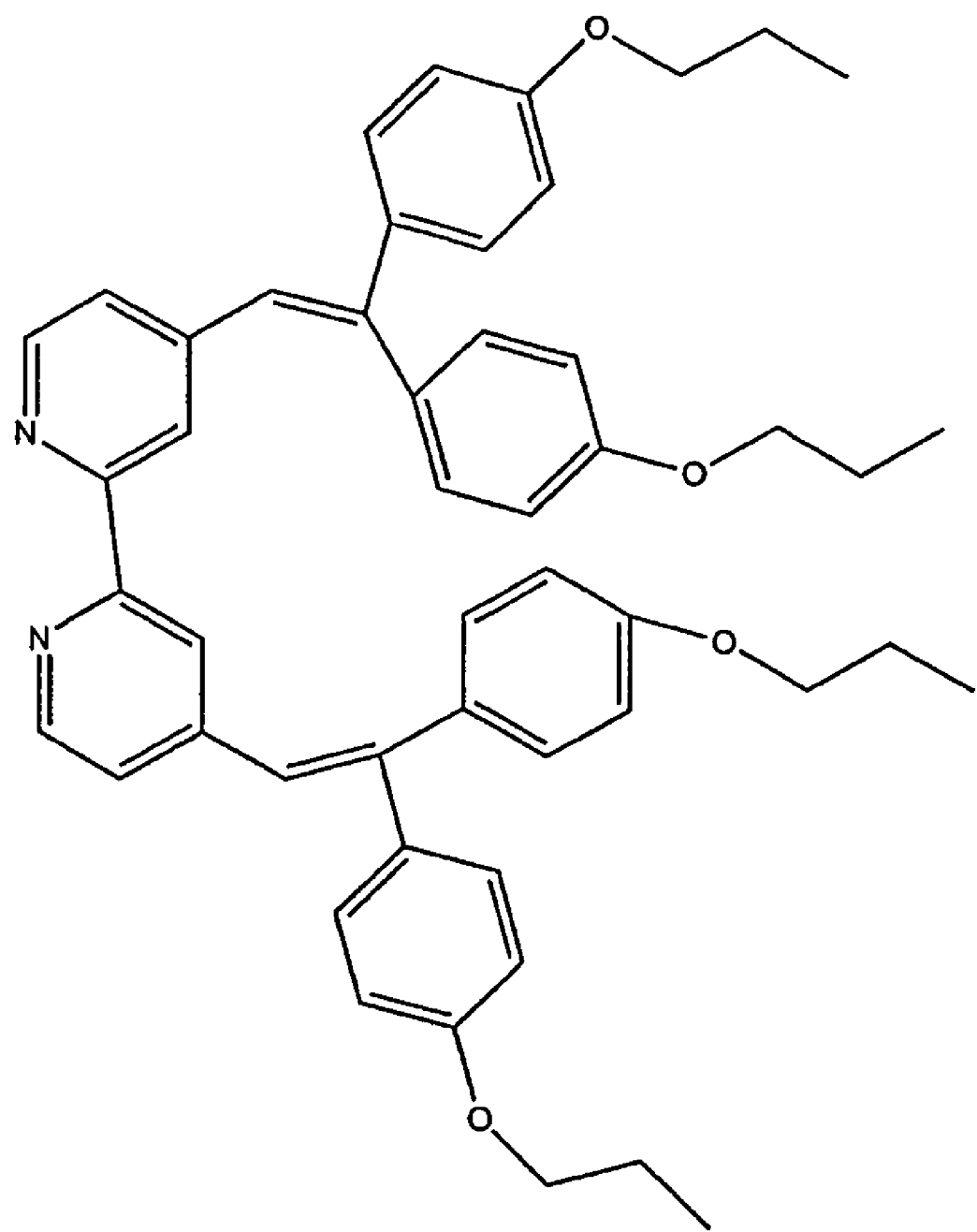

FIG. 9 shows the evolution of photovoltaic parameters of device E at 80° C. in the dark. It is clear that the presence of 1-decylphosphonics has enhanced the stability of photovoltage under the thermal stress at 80° C. FIG. 10 shows the evolution of photovoltaic parameters of device E covered with a UV filter at 55-60° C. under AM 1.5 sunlight (100 mW/cm$^2$).

In conclusion, new heteroleptic polypyridyl ruthenium complexes with high molar extinction coefficients have been synthesized and demonstrated as highly efficient, stable sensitizers for nanocrystalline solar cells. Enhancing the molar extinction coefficient of sensitizers has been demonstrated to be an elegant strategy to improve the photovoltaic performance of dye sensitized solar cells.

The invention claimed is:
1. An organometallic complex of a metal Me selected from the group consisting of Ru, Os and Fe, comprising as a ligand a compound L1, said complex being of formula

Me L1 L(Z)$_2$     (I)

if L1 is a compound of formula (a), (b), (c), (d), (g), (h), (i) or (j)

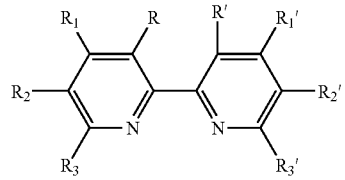
(a)

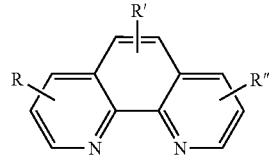
(b)

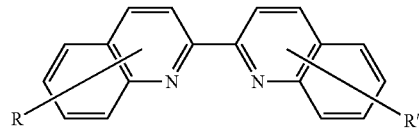
(c)

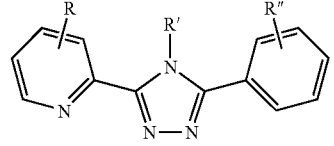
(d)

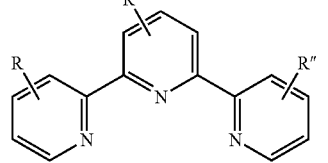
(e)

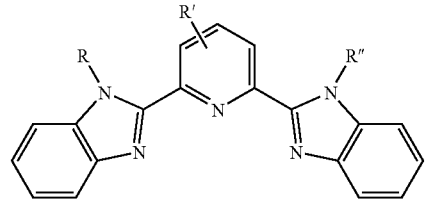
(f)

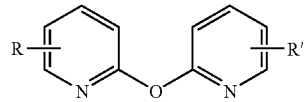
(g)

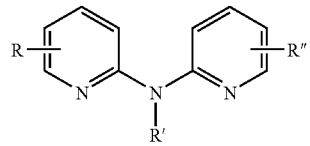
(h)

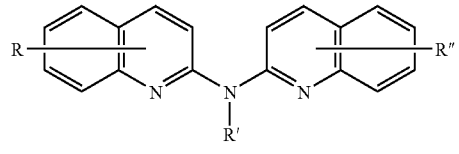
(i)

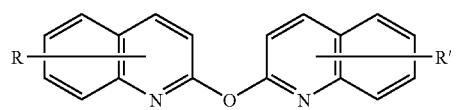
(j)

or of formula

Me L1 LZ    (II)

if L1 is a compound of formula (e) or (f),
 wherein at least one of substituents —R, —R$_1$, —R$_2$, —R$_3$, —R', —R$_1$', —R$_2$', —R$_3$' or —R" is a substituent selected from formula (1), (2) or (3)

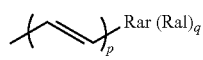    (1)

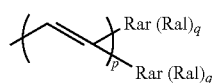    (2)

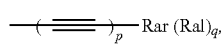    (3)

wherein p is an integer from 1 to 4,
wherein q is an integer from 1 to 4,
wherein Rar is a monocyclic or polycyclic aryl from C6 to C22,
wherein each —Ral is selected from —H, —R1, —(O—R1)$_n$,
—NHR1, —N(R1)$_2$,

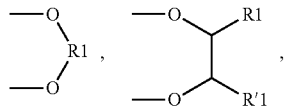

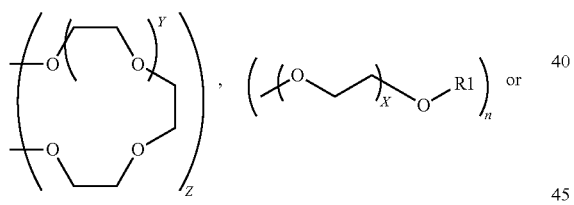

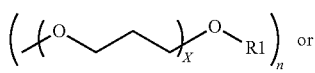

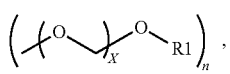

wherein R1, R'1 is an alkyl from 1 to 10 carbon atoms,
wherein X is from 0 to 20,
wherein n is from 0 to 5,
wherein Y is from 1 to 8,
wherein Z is 1 or 2, and
wherein the other one(s) of substituents —R, —R$_1$, —R$_2$, —R$_3$, —R', —R$_1$', —R$_2$', —R$_3$' and/or —R" is (are) the same or a different substituent of formula (1), (2) or (3), or is (are) selected from H, OH, R2, (OR2)$_n$, N(R2)$_2$, a linear polyether or a cyclic polyether, wherein R2 is an alkyl of 1-20 carbon atoms, and wherein 0<n<5;

wherein L is a ligand of formula

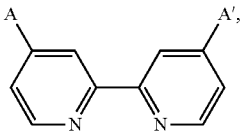    (III)

wherein A and A' are anchoring groups selected from COOH, PO$_3$H$_2$, PO$_4$H$_2$, SO$_3$H$_2$, SO$_4$H$_2$, CONHOH, deprotonated forms thereof or chelating groups with π conducting character; and
wherein Z is selected from the group consisting of H$_2$O, Cl, Br, CN, NCO, NCS and NCSe.

2. The organometallic complex as claimed in claim 1, said complex being of formula Me L1 L(Z)$_2$    (I), wherein Me is selected from the group consisting of Ru, Os and Fe;
wherein L is selected from the group of ligands consisting of

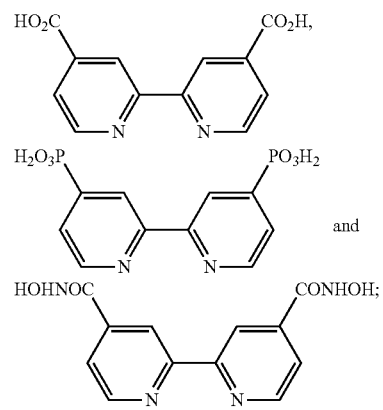

wherein Z is selected from H$_2$O, —Cl, —Br, —CN, —NCO, —NCS or —NCSe; and
wherein L1 is a substituted bipyridine of formula

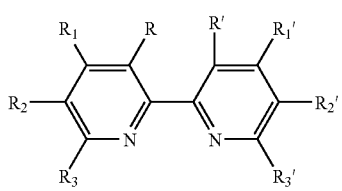    (a)

wherein at least one substituent —R, —R$_1$, —R$_2$, —R$_3$, —R', —R$_1$', —R$_2$' or —R$_3$' is a substituent selected from the group of substituents (1), (2) and (3)

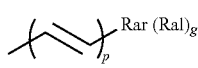    (1)

-continued

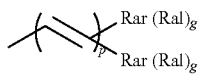     (2)

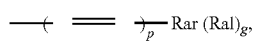     (3)

wherein p is an integer from 1 to 4,
wherein q is an integer from 1 to 4,
wherein Rar is a monocyclic or polycyclic aryl from C6 to C22,
wherein each —Ral is selected from —H, —R1, —(O—R1)$_n$,
—NHR1 or —N(R1)$_2$,

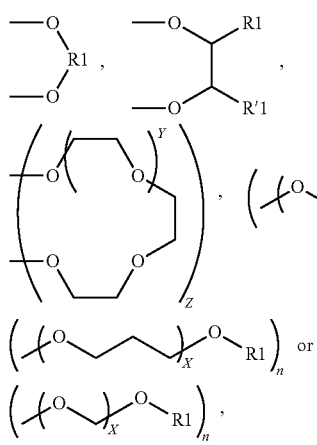

wherein R1, R'1 is an alkyl from 1 to 10 carbon atoms,
wherein X is from 0 to 20,
wherein n is from 0 to 5,
wherein Y is from 1 to 8,
wherein Z is 1 or 2.

3. The organometallic complex as claimed in claim 2, said complex being of formula

     (I), wherein Me is selected from the group consisting of Ru, Os and Fe;
wherein L is selected from the group of ligands consisting of

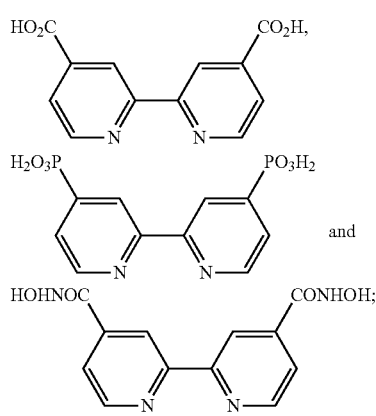

wherein Z is selected from H$_2$O, —Cl, —Br, —CN, —NCO, —NCS or —NCSe; and
wherein L1 is a 4,4'-substituted bipyridine of formula

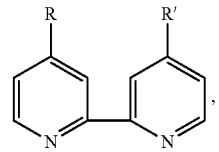     (a')

wherein R and R' are substituents selected from formula (1), (2) or (3)

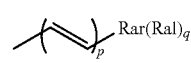     (1)

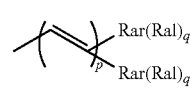     (2)

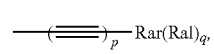     (3)

wherein p is an integer from 1 to 4,
wherein q is an integer from 1 to 4,
wherein Rar is a monocyclic or polycyclic aryl from C6 to C22,
wherein each —Ral is selected from —H, —R1, —(O—R1)$_n$,
—NHR1, —N(R1)$_2$,

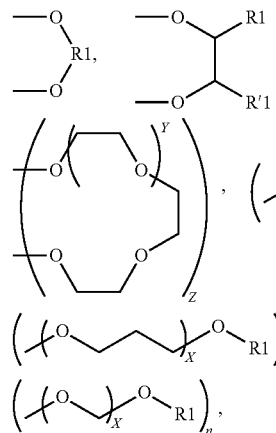

wherein R1, R'1 is an alkyl from 1 to 10 carbon atoms,
wherein X is from 0 to 20,
wherein n is from 0 to 5,
wherein Y is from 1 to 8, and
wherein Z is 1 or 2.

4. The organometallic complex as claimed in claim 3, said complex being of formula

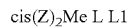

wherein Z is —NCS;
wherein Me is Ru;
wherein L is selected from the group of ligands consisting of

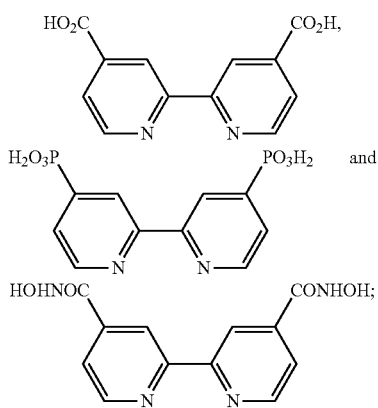

and
wherein L1 is of formula (a')

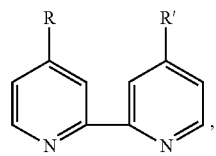

wherein R is a substituent selected from the group consisting of substituents (1), (2) and (3)

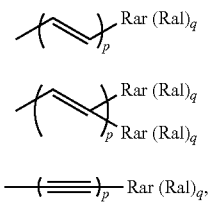

wherein p is 1,
wherein Rar is selected from the group consisting of benzene and naphthalene,
wherein q is from 1 to 4,
wherein Ral is OR1, R1 being selected from an alkyl of 1 to 10 carbon atoms, a linear polyether or a cyclic polyether, and
wherein R' is a substituent selected from formula (1), (2) or (3)

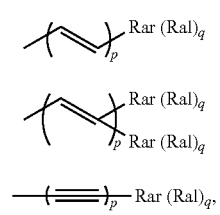

wherein p is an integer from 1 to 4,
wherein q is an integer from 1 to 4,
wherein Rar is a monocyclic or polycyclic aryl from C6 to C22, wherein each —Ral is, independently one from the others, selected from —H, —R1, —(O—R1)$_n$, —NHR1, —N(R1)$_2$,

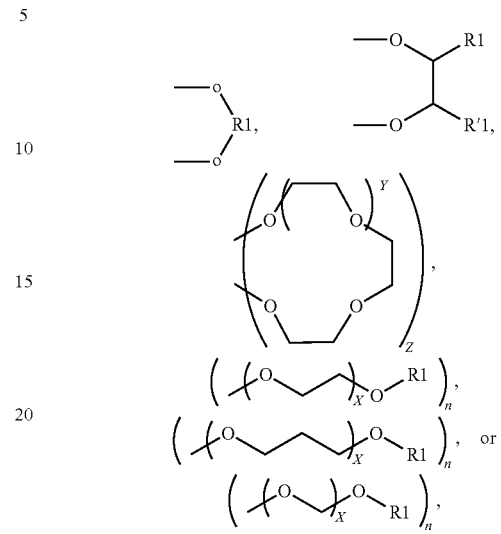

wherein R1, R'1 is an alkyl from 1 to 10 carbon atoms,
wherein X is from 0 to 20,
wherein n is from 0 to 5,
wherein Y is from 1 to 8, and
wherein Z is 1 or 2.

5. A regenerative photoelectrochemical cell comprising a photoanode, said photoanode comprising at least one semi-conductive metal oxide layer on a conductive substrate, sensitized by a photosensitizing dye, a counter electrode and an electrolyte arranged between said semi-conductive metal oxide layer and said counter electrode, wherein said photosensitizing dye is an organometallic complex as claimed in claim 1.

6. A cell as claimed in claim 5, wherein an amphiphilic compacting compound whose molecular structure comprises at least one anchoring group, a hydrophobic portion and a terminal group is co-adsorbed with said photosensitizing dye on said semi-conductive metal oxide layer in a mixed monolayer.

7. A cell as claimed in claim 6, wherein said compacting compound is selected from the group consisting of alkyl carboxylic acids, alkyl dicarboxylic acids, alkyl carboxylates, alkyl phosphonic acids, alkyl phosphonates, alkyl diphosphonic acids, alkyl diphosphonates, alkyl sulphonic acids, alkyl sulphonates, alkyl hydroxamic acids and alkyl hydroxamates, wherein said alkyl is linear or branched from C1 to C20.

8. A cell as claimed in claim 6 or 7, wherein the molar ratio of said photosensitizing dye to said co-adsorbed compacting compound is of between 10 and ½, and in that said self-assembled monolayer is a dense packed monolayer having an order-disorder transition temperature above 80° C.

9. A cell as claimed in claim 6, wherein the length of said hydrophobic chain portion of the compacting compound allows said terminal group to protrude above the sensitizing dye in said monolayer.

10. A cell as claimed in claim 5, wherein said electrolyte comprises a redox system, that said redox system comprises an electrochemically active salt and a first compound forming a redox couple with either the anion or the cation of said electrochemically active salt, wherein said salt is a room temperature molten salt, said molten salt being liquid at least between standard room temperature and 80° C. above said room temperature.

11. A cell as claimed in claim 5, wherein said electrolyte further comprises a polar organic solvent having a boiling point of 100° C. or greater than 100° C. at normal atmospheric pressure.

12. A cell as claimed in claim 11, wherein said solvent is a nitrile selected from 3-methoxypropionitrile 3-ethoxypropionitrile,3-butoxupropionitrile, and butyronitrile.

13. A cell as claimed in claim 5, wherein said electrolyte further comprises, as an additive, a compound formed by a neutral molecule comprising one or more nitrogen atom(s) with a lone electron pair.

14. A cell as claimed in claim 13, wherein said neutral molecule has following formula:

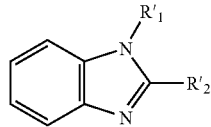

wherein $R'_1$ and $R'_2$ can be H, alkyl, alkenyl, alkynyl, alkoxyl, poly-ether, and/or phenyl, independently one from the other, the number of carbon atoms of each substituent ranging from 1 to 20, the substituent being linear or branched.

15. A method of preparing a dye-sensitized solar cell; the method comprising
the step of providing a dye comprising at least one compound L1 of formula (a), (a'), (b), (c), (d), (e), (f), (g), (h), (i), or (j) as defined in claims 1 and 3,
wherein at least one of —R, —$R_1$, —$R_2$, —$R_3$, —R', —$R_1$', —$R_2$', —$R_3$' or —R" is a substituent selected from formula (1), (2) or (3)

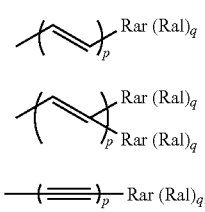

wherein p is an integer from 1 to 4,
wherein q is an integer from 1 to 4,
wherein Rar is a monocyclic or polycyclic aryl from C6 to C22,
wherein each —Ral is selected from —H, —R1, —(O—R1)$_n$, —NHR1 or —N(R1)$_2$,

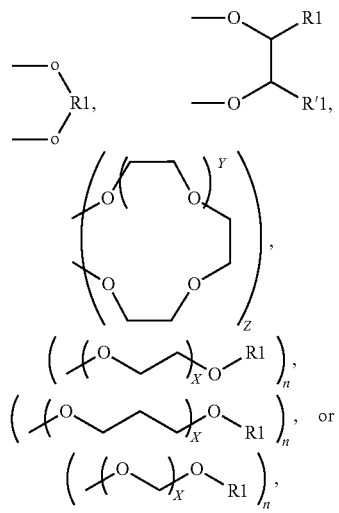

wherein R1, R'1 is an alkyl from 1 to 10 carbon atoms,
wherein X is from 0 to 20,
wherein n is from 0 to 5,
wherein Y is from 1 to 8, and
wherein Z is 1 or 2, and
wherein the other one(s) of substituents —R, —$R_1$, —$R_2$, —$R_3$, —R', —$R_1$', —$R_2$', —$R_3$' and/or —R" is (are) the same or a different substituent of formula (1), (2) or (3), or is (are) selected from H, OH, R2, (OR2)$_n$, N(R2)$_2$, a linear polyether or a cyclic polyether, wherein R2 is an alkyl of 1-20 carbon atoms, and wherein 0<n<5; and
the step of preparing the solar cell comprising said dye.

16. Cis-dithiocyanato-(2,2'-bipyridyl-4,4'-dicarboxylate)-[4,4'-bis(4-hexyloxystyryl)-2,2'bipyridyl]-Ru(II).

17. 4,4'-bis(4-hexyloxystyryl)-2,2'bipyridine.

* * * * *

UNITED STATES PATENT AND TRADEMARK OFFICE
CERTIFICATE OF CORRECTION

| | | |
|---|---|---|
| PATENT NO. | : 7,932,404 B2 | Page 1 of 1 |
| APPLICATION NO. | : 11/658780 | |
| DATED | : April 26, 2011 | |
| INVENTOR(S) | : Shaik Mohammad Zakeeruddin et al. | |

It is certified that error appears in the above-identified patent and that said Letters Patent is hereby corrected as shown below:

Please correct the following:

1. Column 4, line 20: in the formula, the line for the bond shall cross only the bracket "[" and not the leg of "Π" and "al" in "Ral" shall not be in italic: the correct formula is "–R=[Π]–(Ral)$_q$";

2. Column 15, line 14: same correction as 1. above;

3. Column 15, line 21: "nitrites" shall be corrected to "nitriles";

4. Column 18, lines 26-27: "Synthesized According to Procedure Published" shall be corrected with non-capital letters to "synthesized according to procedure published";

5. Column 21, lines 7 and 22: "K 60" shall be corrected to "K60" (without space between K and 60);

6. From column 26, line 62, formula of substituent (1), to column 27, line 8, formula of substituent (3): in all three formulae, the subscript "$_g$" shall be corrected to subscript "$_q$" and in formula (3), the double bond shall be corrected to a triple bond. These formulae are the same as those written down in column 25, lines 10-20;

7. Column 29, between lines 5 and 10: the word "and" between the first formula and the second formula shall be moved to between the second formula and the third formula;

8. Column 29, after line 60: in the formula (3), the "," at the end of said formula provides confusion, since it seems that the subscript "$_q$" is "$_{q,}$" with the meaning "$_{q'}$". The "," shall be removed from the formula;

9. Column 31, line 29: ";" after "cell" shall be replaced by a ",".

Signed and Sealed this
Second Day of August, 2011

David J. Kappos
*Director of the United States Patent and Trademark Office*